United States Patent
Fallin et al.

(10) Patent No.: US 10,743,995 B2
(45) Date of Patent: Aug. 18, 2020

(54) ORTHOPEDIC FASTERNERS, INSTRUMENTS AND METHODS

(71) Applicant: First Ray, LLC, Logan, UT (US)

(72) Inventors: T. Wade Fallin, Hyde Park, UT (US); Daniel J. Triplett, Providence, UT (US)

(73) Assignee: First Ray, LLC, Logan, UT (US)

( * ) Notice: Subject to any disclaimer, the term of this patent is extended or adjusted under 35 U.S.C. 154(b) by 220 days.

(21) Appl. No.: 15/912,346

(22) Filed: Mar. 5, 2018

(65) Prior Publication Data

US 2018/0193151 A1 Jul. 12, 2018

Related U.S. Application Data

(63) Continuation-in-part of application No. 15/194,108, filed on Jun. 27, 2016, now abandoned.
(Continued)

(51) Int. Cl.
| | |
|---|---|
| *A61B 17/68* | (2006.01) |
| *A61F 2/30* | (2006.01) |
| *A61B 17/88* | (2006.01) |
| *A61B 17/80* | (2006.01) |
| *A61F 2/44* | (2006.01) |

(Continued)

(52) U.S. Cl.
CPC .......... *A61F 2/30724* (2013.01); *A61B 17/68* (2013.01); *A61B 17/7059* (2013.01); *A61B 17/8004* (2013.01); *A61B 17/808* (2013.01); *A61B 17/809* (2013.01); *A61B 17/8061* (2013.01); *A61B 17/8095* (2013.01); *A61B 17/8872* (2013.01); *A61F 2/30749* (2013.01); *A61F 2/389* (2013.01); *A61F 2/3859* (2013.01); *A61F 2/4465* (2013.01); *A61B 17/0642* (2013.01); *A61B 17/15* (2013.01); *A61B 17/151* (2013.01); *A61B 17/17* (2013.01); *A61B 2017/681* (2013.01); *A61F 2002/30576* (2013.01); *A61F 2002/30884* (2013.01)

(58) Field of Classification Search
CPC ................... A61B 17/15; A61B 17/17; A61B 17/1717–1725; A61B 17/66; A61B 17/7216; A61B 17/7225; A61B 2017/90; A61B 2017/681
See application file for complete search history.

(56) References Cited

U.S. PATENT DOCUMENTS

| | | | | |
|---|---|---|---|---|
| 4,929,247 | A * | 5/1990 | Rayhack | A61B 17/8019 606/105 |
| 5,540,695 | A * | 7/1996 | Levy | A61B 17/15 606/87 |
| 5,951,557 | A * | 9/1999 | Luter | A61B 17/80 606/286 |
| 7,540,874 | B2 * | 6/2009 | Trumble | A61B 17/15 606/105 |

(Continued)

FOREIGN PATENT DOCUMENTS

| | | |
|---|---|---|
| WO | WO 00/64360 A2 | 11/2000 |
| WO | WO 2006/122194 A1 | 11/2006 |
| WO | WO 2010/028045 A1 | 3/2010 |

OTHER PUBLICATIONS

Supplementary European Search Report dated Feb. 27, 2019 for corresponding European Patent Application No. EP16818699.

*Primary Examiner* — Zade Coley
(74) *Attorney, Agent, or Firm* — David Meibos; Maywood IP Law

(57) ABSTRACT

Examples of the invention relate to methods, implants, and instruments for compressing first and second bone portions or a bone portion and an implant together.

20 Claims, 33 Drawing Sheets

Related U.S. Application Data

(60) Provisional application No. 62/465,289, filed on Mar. 1, 2017, provisional application No. 62/188,185, filed on Jul. 2, 2015, provisional application No. 62/308,011, filed on Mar. 14, 2016.

(51) Int. Cl.
*A61B 17/70* (2006.01)
*A61F 2/38* (2006.01)
*A61B 17/064* (2006.01)
*A61B 17/15* (2006.01)
*A61B 17/17* (2006.01)

(56) References Cited

U.S. PATENT DOCUMENTS

| | | | |
|---|---|---|---|
| 9,113,969 B2* | 8/2015 | Niederberger | A61B 17/8019 |
| 2005/0277941 A1* | 12/2005 | Trumble | A61B 17/15 |
| | | | 606/79 |
| 2012/0253410 A1* | 10/2012 | Taylor | A61B 17/6458 |
| | | | 606/329 |
| 2012/0271314 A1* | 10/2012 | Stemniski | A61B 17/15 |
| | | | 606/87 |
| 2013/0144343 A1 | 6/2013 | Arnett et al. | |
| 2013/0150900 A1* | 6/2013 | Haddad | A61B 17/809 |
| | | | 606/290 |
| 2013/0231668 A1* | 9/2013 | Olsen | A61B 17/151 |
| | | | 606/79 |
| 2014/0031827 A1* | 1/2014 | Lancianese | A61B 17/15 |
| | | | 606/87 |
| 2017/0000533 A1* | 1/2017 | Fallin | A61B 17/7059 |
| 2017/0000537 A1* | 1/2017 | Fallin | A61B 17/7059 |

* cited by examiner

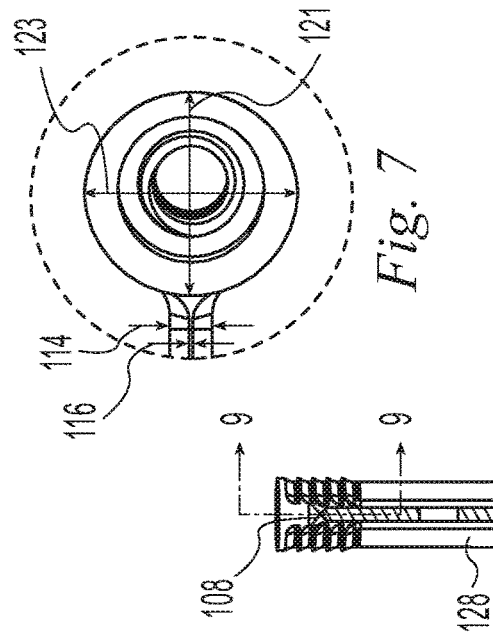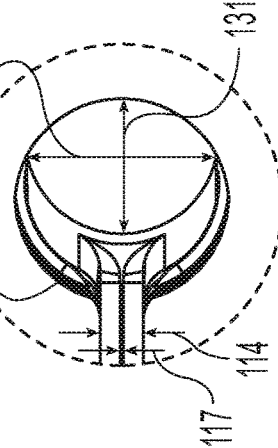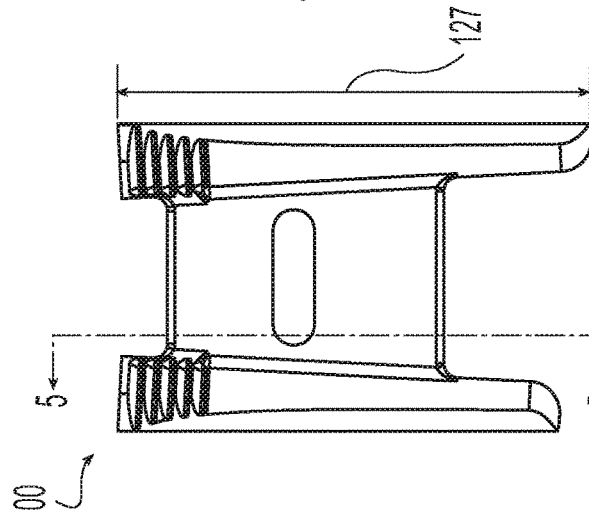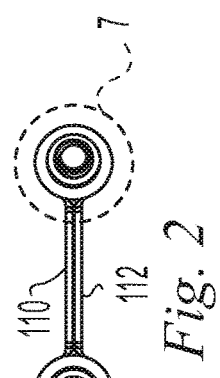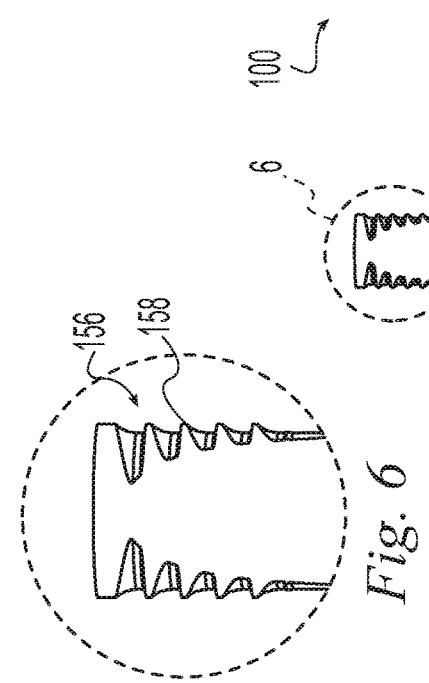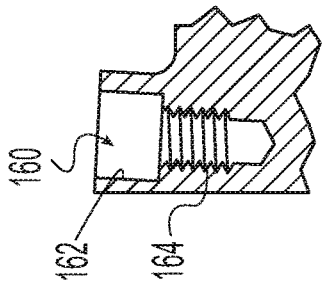

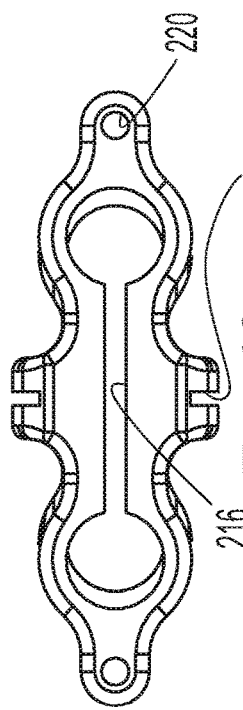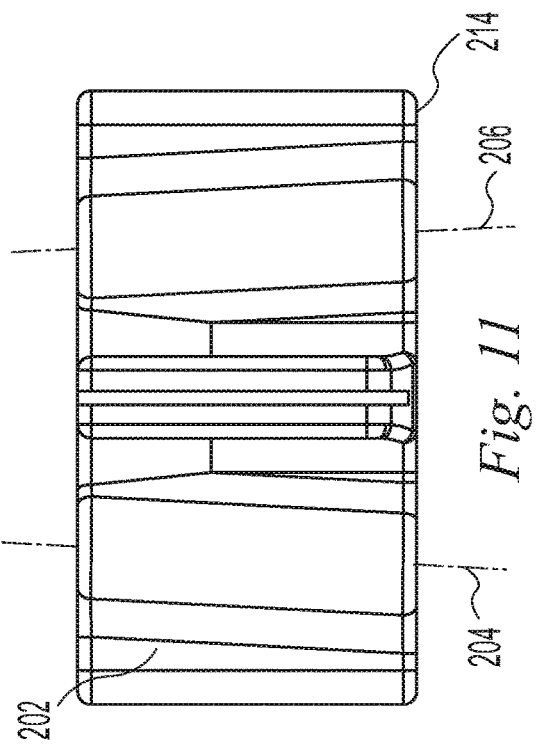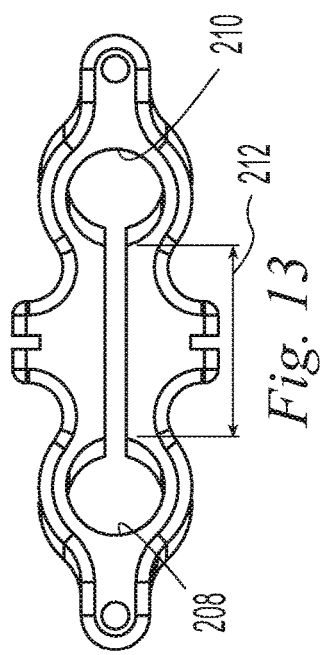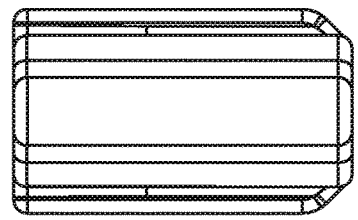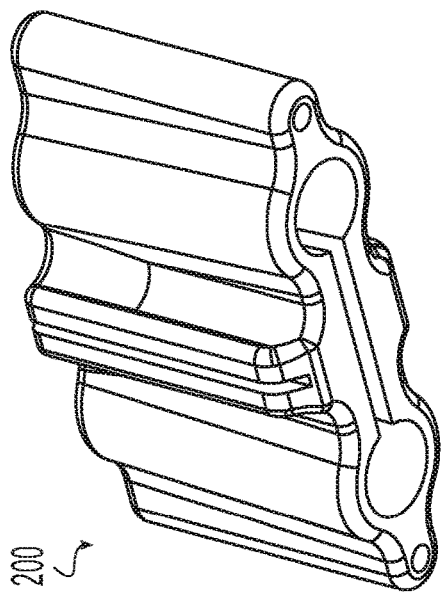

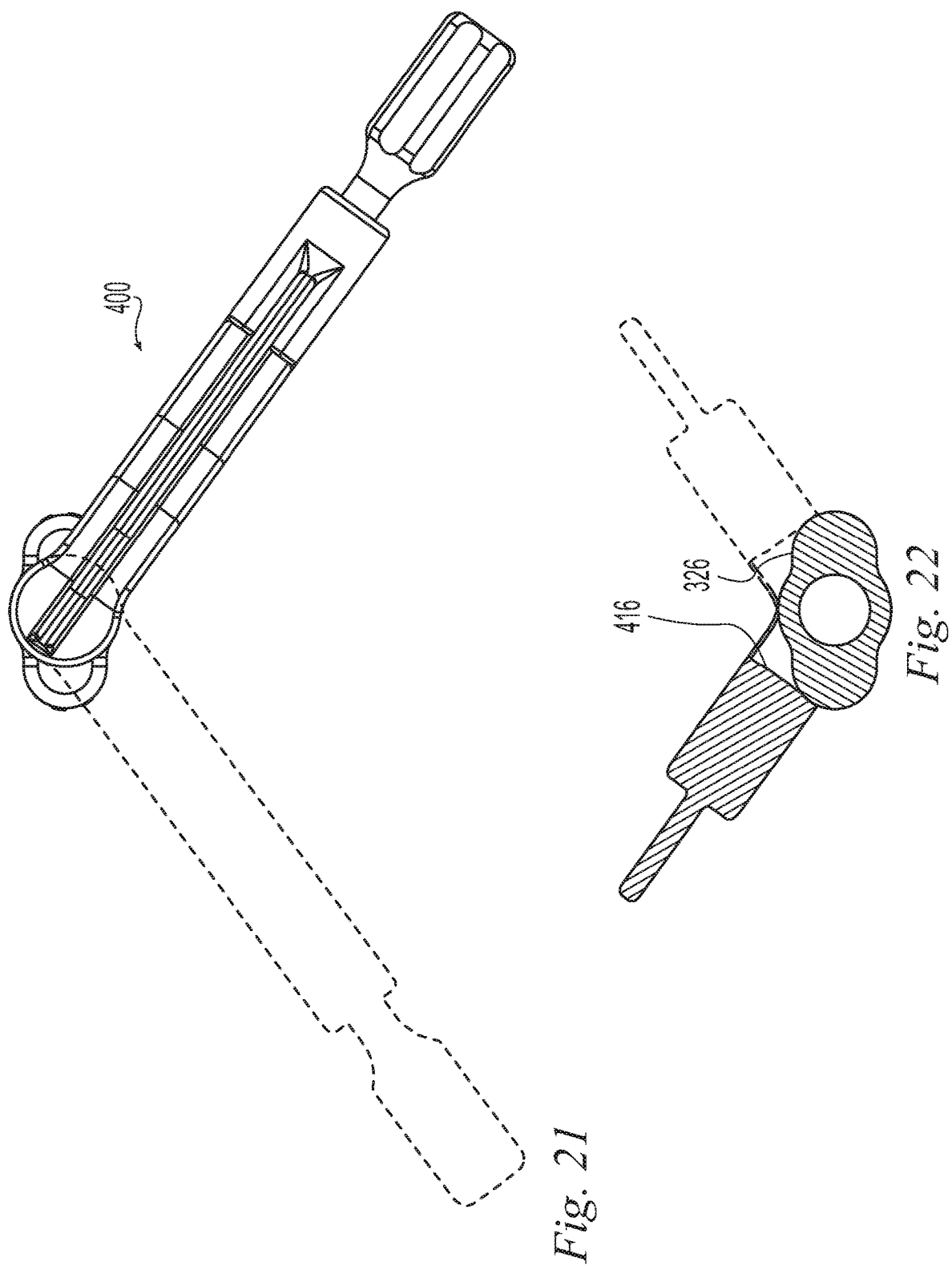

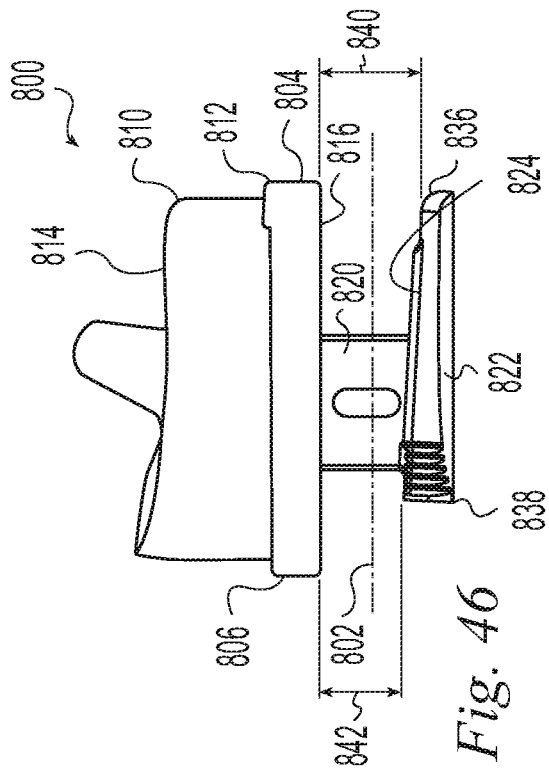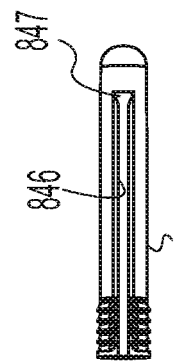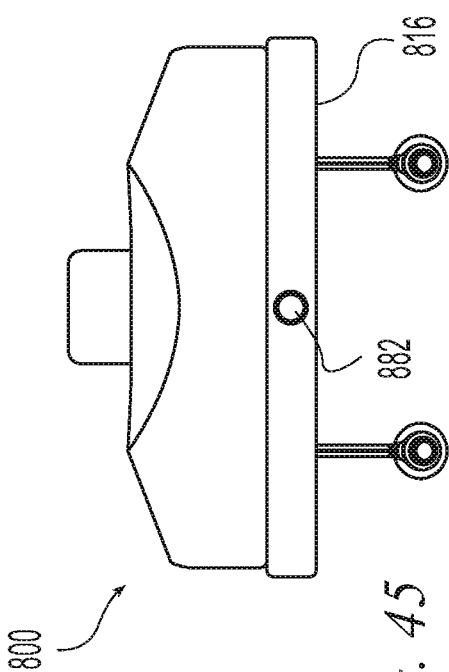
Fig. 45
Fig. 46
Fig. 47

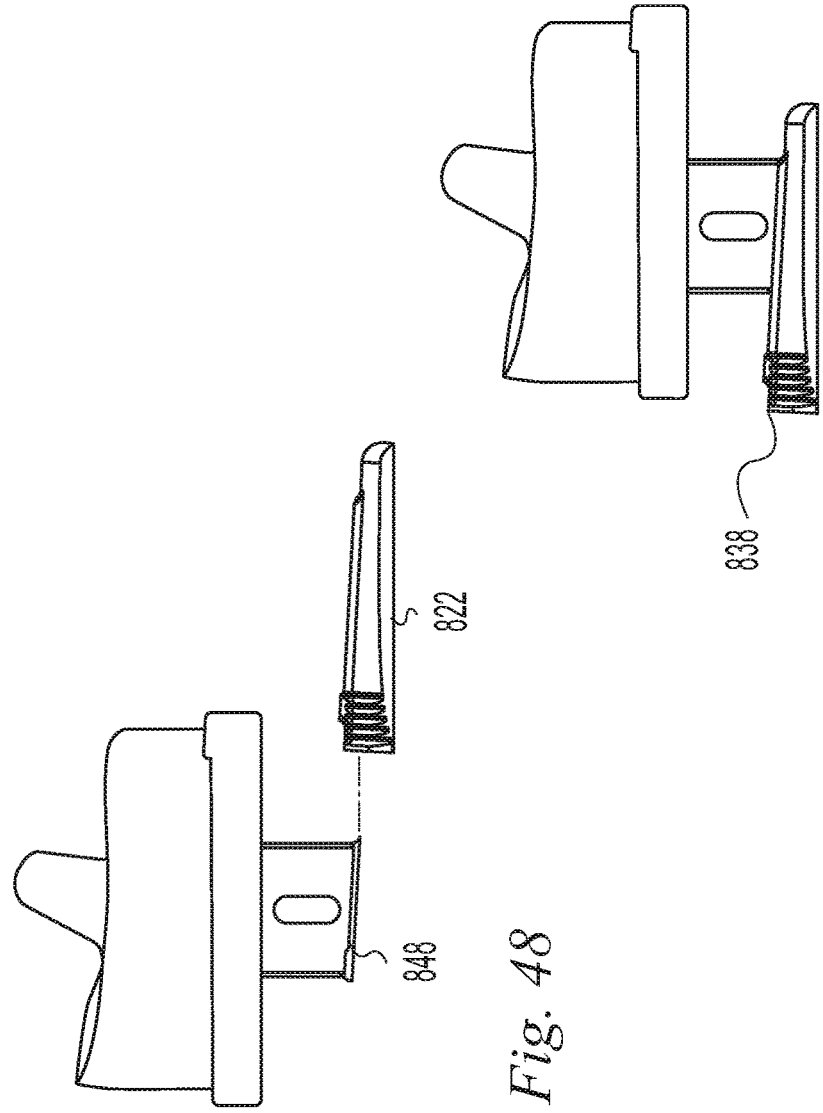
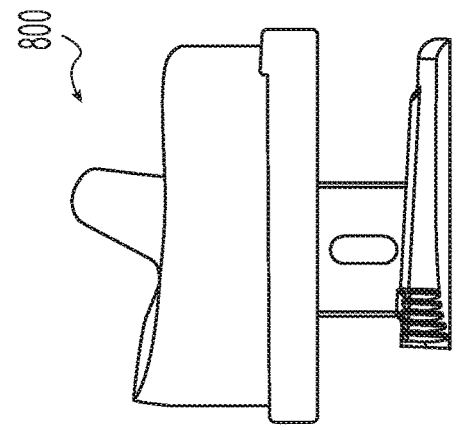
Fig. 48
Fig. 49
Fig. 50

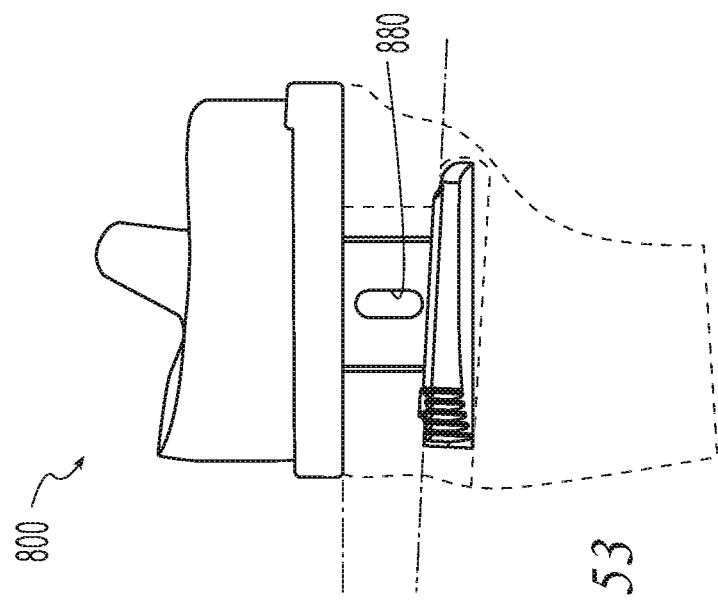
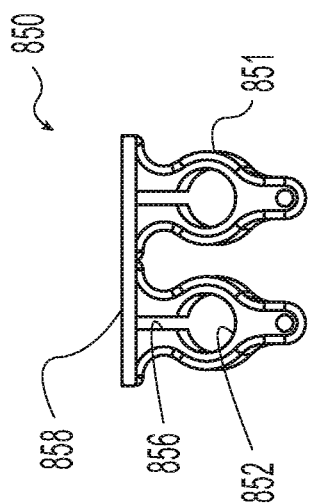
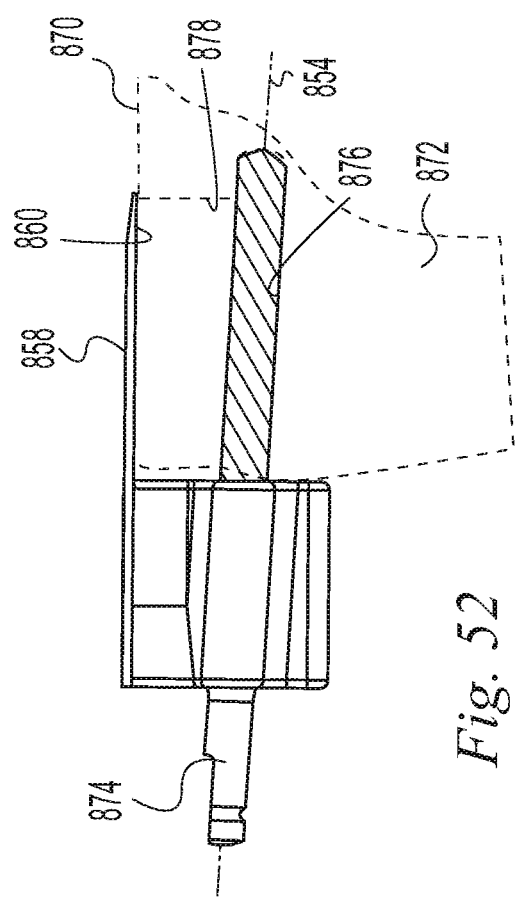
Fig. 51
Fig. 52
Fig. 53

ORTHOPEDIC FASTERNERS, INSTRUMENTS AND METHODS

CROSS-REFERENCE TO RELATED APPLICATIONS

This application claims the benefit of U.S. Provisional Patent Application Ser. No. 62/465,289, filed Mar. 1, 2017, titled ORTHOPEDIC FASTENERS, INSTRUMENTS AND METHODS, which is incorporated by reference as though set forth herein in its entirety.

This application is also a continuation-in-part of U.S. patent application Ser. No. 15/194,108, filed Jun. 27, 2016, titled COMPRESSION IMPLANTS, INSTRUMENTS, AND METHODS, which claims the benefit of U.S. Provisional Patent Application Ser. No. 62/188,185, filed Jul. 2, 2015, titled ORTHOPEDIC FASTENER, INSTRUMENT, AND METHOD, and U.S. Provisional Patent Application Ser. No. 62/308,011, filed Mar. 14, 2016, titled COMPRESSION IMPLANTS, INSTRUMENTS, AND METHODS, all of which are incorporated by references as though set forth herein in their entirety.

FIELD OF THE INVENTION

Examples of the invention relate to methods, implants, and instruments for compressing first and second bone portions or a bone portion and an implant together.

BACKGROUND

Various conditions may affect skeletal joints such as the deterioration, elongation, shortening, or rupture of soft tissues, cartilage, and/or bone associated with the joint and consequent laxity, pain, and/or deformity. It may be desirable to change the angular alignment of a bone or a portion of a bone to restore function and/or reduce pain. It likewise may be desirable to fuse a joint to fix the bones of the joint in a better angular alignment or reduce pain caused by motion at the joint. It may also be desirable to support a fractured bone to allow healing of the fracture to occur. It may also be desirable to support an implant on a bone. To this end, various osteotomy procedures, joint fusion procedures, fracture fixation procedures, joint resurfacing procedures, implants and instruments have been proposed. Such procedures have been performed throughout the body to make various angular adjustments in, fuse joints associated with, fuse fractures associated with, and/or resurface articular surfaces of tibia, fibula, femur, pelvis, humerus, ulna, radius, carpal, metacarpal, tarsal, metatarsal, phalangeal and other bones.

SUMMARY

Examples of the invention provide methods, implants, and instruments capable of compressing first and second bone portions or a bone portion and an implant together. The bone portions may be portions of the same bone as in a fracture or osteotomy. The bone portions may be portions of different bones as in arthrodesis. A bone portion may be a portion of a bone adjacent an articulating joint and the implant may be a resurfacing implant, a spacer, and/or a fusion supporting implant.

BRIEF DESCRIPTION OF THE DRAWINGS

Various examples of the invention will be discussed with reference to the appended drawings. These drawings depict only illustrative examples of the invention and are not to be considered limiting of its scope.

FIG. 1A is front elevation view of a bone implant according to one example of the invention;
FIG. 2 is a top view of the bone implant of FIG. 1;
FIG. 3 bottom view of the bone implant of FIG. 1;
FIG. 4 is a side elevation view of the bone implant of FIG. 1;
FIG. 5 is a cross sectional view of the bone implant of FIG. 1 taken along line 5-5 of FIG. 1A;
FIG. 6 is a detail view of the bone implant of FIG. 1;
FIG. 7 is a detail view of the bone implant of FIG. 1;
FIG. 8 is a detail view of the bone implant of FIG. 1;
FIG. 9 is a detail view of the bone implant of FIG. 1;
FIG. 10 is a perspective view of an example of a hole forming guide for the bone implant of FIG. 1;
FIG. 11 is a front elevation view of the hole forming guide of FIG. 10;
FIG. 12 is a top view of the hole forming guide of FIG. 10;
FIG. 13 is a bottom view of the hole forming guide of FIG. 10;
FIG. 14 is a side elevation view of the hole forming guide of FIG. 10;
FIG. 21 is a top view of the fixation guide of FIG. 19 with the inserter of FIG. 15 and the implant of FIG. 1 illustrating range of motion;
FIG. 22 is a cross sectional view taken along line 22-22 of FIG. 20 and illustrating range of motion;
FIG. 45 is a front elevation view of an implant according to one example of the invention;
FIG. 46 is a side elevation view of the implant of FIG. 45;
FIG. 47 is a top plan view of component 822 of the implant of FIG. 45;
FIGS. 48-50 are side elevation views of the implant of FIG. 45 illustrating the motion of component 822;
FIG. 51 is a front elevation view of an example of a hole forming guide for the implant of FIG. 45;
FIG. 52 is a side elevation view of the guide of FIG. 51;
FIG. 53 is a side elevation view of the implant of FIG. 45 mounted on a bone.

DESCRIPTION OF THE ILLUSTRATIVE EXAMPLES

Figure 1B:
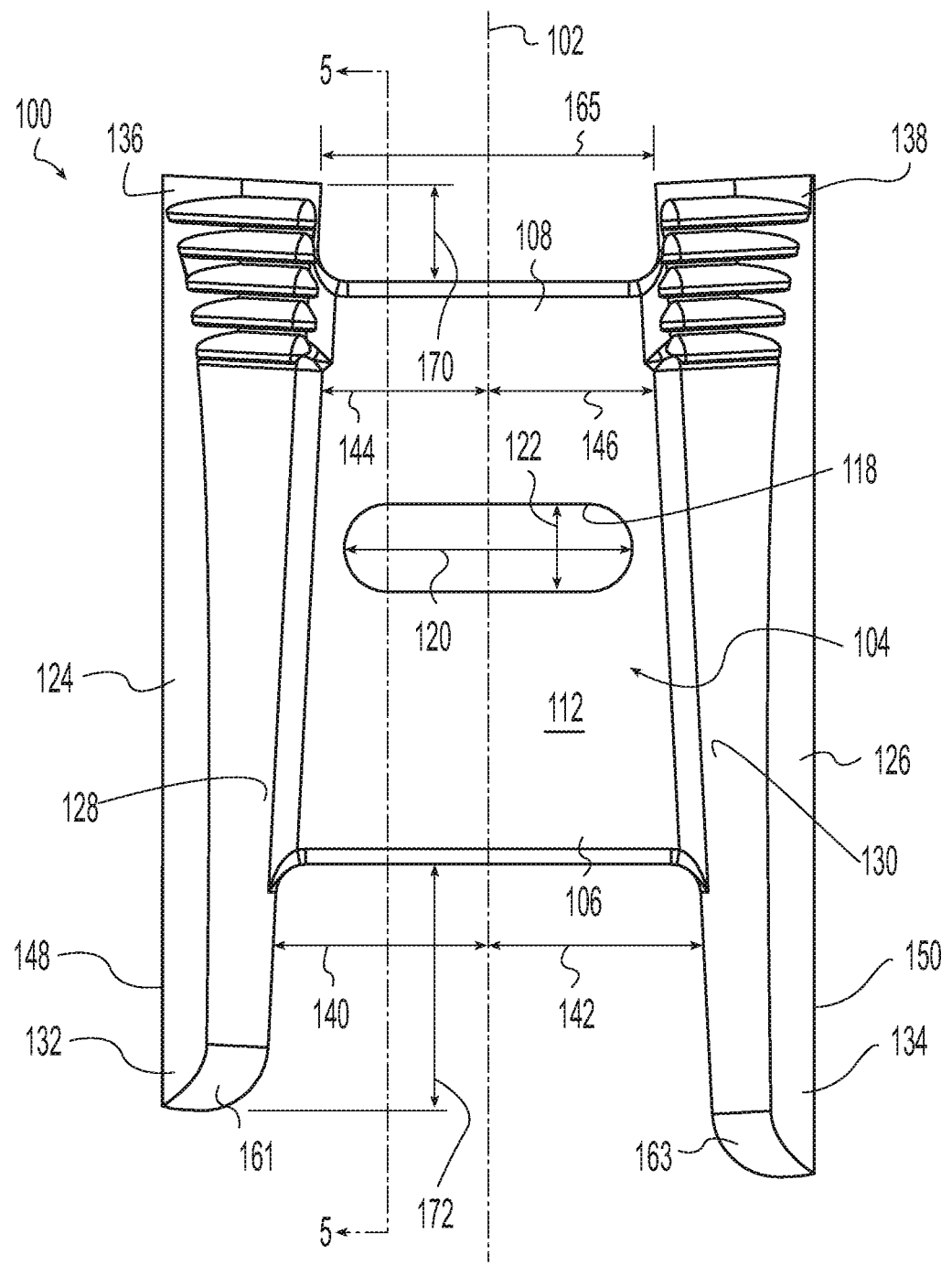
FIG. 1B is an enlarged front elevation view of the bone implant of FIG. 1.

The following illustrative examples describe methods, implants, and instruments capable of compressing first and second bone portions or a bone portion and an implant together. The bone portions may be portions of the same bone that have become separated due to a fracture or an osteotomy. The bone portions may be portions of different bones as in an arthrodesis performed to fuse a joint. A bone portion may be a portion of a bone adjacent an articulating joint and the implant may be a resurfacing implant, a spacer, and/or a fusion supporting implant. Examples of the invention may be used with any bone or joint including but not limited to bones such as a tibia, fibula, femur, pelvis, humerus, ulna, radius, carpal, metacarpal, tarsal, metatarsal, phalange and joints associated therewith.

The term "transverse" is used herein to mean crossing as in non-parallel.

Examples according to the invention provide methods, implants, and instruments capable of compressing first and second bone portions or a bone portion and an implant together. FIGS. 1-9 illustrate an example in the form of a fastener 100 for joining first and second bone portions. The fastener includes an insertion axis 102 along which the fastener moves as it is inserted into or removed from a bone. The fastener 100 has a body 104 extending between a body distal or leading end 106 and a body proximal or trailing end 108. The body leading end 106 and the body trailing end 108 are spaced from one another longitudinally relative to the insertion axis. In the illustrative example of FIGS. 1-9, the body 104 has a generally planar configuration with opposed planar sides 110, 112 spaced apart a body thickness 114. The opposed planar sides 110, 112 converge toward the body trailing end 108 to define a trailing edge having a trailing edge thickness 116 that is less than the body thickness 114 (FIG. 7). The relatively narrow trailing edge thickness 116 facilitates removal of the fastener 100 after bone has healed over the body trailing end 108. During removal, such as in a revision procedure, the narrow trailing edge will cut through overlying bone. In the illustrative example of FIGS. 1-9, the opposed planar sides 110, 112 also converge toward the body leading end 106 to define a leading edge having a leading edge thickness 117 that is less than the body thickness 114. The relatively narrow leading edge thickness 117 facilitates insertion of the fastener 100.

In the illustrative example of FIGS. 1-9, the body 104 has an aperture 118 extending through the body 104 between the opposed planar sides 110, 112. The aperture 118 has a length 120 and a width 122. In the illustrative example of FIGS. 1-9, the aperture length 120 is greater than the aperture width 122 and the aperture length 120 is oriented transverse to the insertion axis 102. In the illustrative example of FIGS. 1-9, the aperture length is oriented normal to the insertion axis. The inclusion of an aperture and its size and orientation are determined for the particular application in which the fastener is to be used. For example, the aperture may receive a fixation member, such as screw 636 in FIG. 36, to provide cross fixation of the bone portions and to prevent the fastener 100 from migrating out of the bone.

The fastener 100 includes first and second legs 124, 126 connected to the body. The legs have a width 121, a depth 123 (FIG. 7), and a length 127 (FIG. 1A). The first and second legs may be the same size or they may be different sizes to accommodate particular anatomy. For example, the legs may have the same width and depth but have different lengths so that they can accommodate bi-cortical fixation in bone portions of varying thickness. Each leg has an elongate inboard surface 128, 130 facing the insertion axis 102 and extending from a leading end 132, 134 to a trailing end 136, 138. The elongate inboard surface 128, 130 is spaced from the insertion axis 102 a leading distance 140, 142 near the leading end and the elongate inboard surface is spaced from the insertion axis 102 a trailing distance 144, 146 near the trailing end. The leading distance 140, 142 and trailing distance 144, 146 for each leg may be equal such that the inboard surface is parallel to the insertion axis 102. The leading distance 140, 142 and trailing distance 144, 146 for each leg may be unequal such that, for example, one or both of the leg inboard surfaces may converge or diverge distally from the insertion axis 102. Preferably, at least one of the leading distances 140, 142 is greater than the corresponding trailing distance 144, 146 and the other leading distance 140, 142 is equal to or greater than the corresponding trailing distance 144, 146 such that the inboard surfaces 128, 130 diverge relative to one another distally or in other words in the leading direction defined by the leading ends and at least one diverges from the insertion axis 102. In the illustrative example of FIGS. 1-9, each leg diverges from the insertion axis 102 in the leading direction. Preferably the inboard surfaces 128, 130 each diverges from the insertion axis 102 by a divergence angle. The included angle between the inboard surfaces 128, 130 is the sum of the individual divergence angles. As described above, the may diverge symmetrically or asymmetrically. The individual divergence angles are preferably in the range of 1-5 degrees. In the illustrative example of FIGS. 1-9, the divergence angles are each 3 degrees yielding an included angle of 6 degrees. When the legs are positioned in bone, the projected area of each leg perpendicular to the insertion axis affects the resistance of the leg to pulling through the bone. The larger the projected area the greater the pull through strength. For a given leg length, the area is determined by the leg depth, or for a cylindrical leg by its diameter. The body is inserted into a slot formed in the bone between the legs. As the slot width increases relative to the leg projected area, the resistance of the leg to being pulled into the slot decreases. Thus, a thinner body and consequently thinner slot increases pull through strength. This can be expressed in terms of the difference between the leg depth and body thickness or in terms of a ratio of leg depth to body thickness.

In the illustrative example of FIGS. 1-9, each leg 124, 126 further includes an elongate outboard surface 148, 150 facing away from the insertion axis 102 and extending from the leading end to the trailing end. In the illustrative example of FIGS. 1-9, the elongate outboard surfaces 148, 150 are parallel to one another and the insertion axis 102.

In the illustrative example of FIGS. 1-9, the fastener legs 124, 126 have a generally elliptical cross section. Near the trailing end the cross section is approximately circular. Near the distal end, the legs are non-circular having a major diameter 129 greater than a minor diameter 131 (FIG. 8). In the illustrative example of FIGS. 1-9, the leg shape can be describes as being a pair of cylinders that diverge toward the leading end with material removed on the outboard surfaces so that the outboard surfaces are rendered parallel. The resulting legs are circular at the trailing end as seen in FIG. 7 and transition into the shape of intersecting circles as the material is removed, becoming narrower, i.e. tapering, in the minor axis toward the leading end as seen in FIG. 8. The front 152 and back 154 of each leg are parallel as seen in FIG. 4. The trailing end of each leg includes barbs 156 as seen in FIG. 6. The barbs 156 are generally in the form of upwardly swept circular projections 158 on the front, back and inboard surfaces of the trailing portion of the leg such as would result if the barbs were circular projections surrounding divergent cylindrical legs and material was removed on the outboard surfaces so that the outboard surfaces were rendered parallel and consequently reeving progressively more of the circular projections in the leading direction. Alternatively, the barbs may extend completely around the circumference of the leg. The trailing ends of the legs include a cavity 160 (FIG. 9) operable to couple with an inserter as described below. Preferably the cavity is threaded to receive a threaded connector. In the illustrative example of FIGS. 1-9, the cavity 160 is a stepped cylindrical cavity with a larger diameter trailing portion 162 and a smaller diameter, threaded leading portion 164. The leading end of each leg includes a radius 161, 163 to ease insertion of the fastener 100 into holes formed in bone. The inboard surfaces 128, 130 of the legs have an inboard surface trailing end spacing 165 at the trailing end of the legs. The trailing end of the body 108 is recessed toward the leading end of the legs by a trailing end recess distance 170. The leading end of the body 106 is recessed toward the trailing end of the legs by a leading end recess distance 172. The recess distances 170, 172 are preferably equal to or greater than a bone cortex thickness at a location at which the fastener is to be used so that the body 104 is located inward of the cortical bone when the fastener is installed.

The various sizes and proportions for the fastener will vary based on the application. For example, depending on the application, leg depth preferably ranges from 2 mm to 7 mm and the body thickness preferably ranges from 0.5-5 mm. Further for example, in many applications, such as for use in the mid and fore regions of the hands and feet, a fastener may advantageously have a leg depth of 2.5-4.5 mm and a body thickness of 0.5-1.5 mm. The ratio of leg depth to body thickness preferably ranges from 14:1 to 1.5:1. More preferably, the ratio ranges from 5:1 to 3:1.

In the illustrative example of FIGS. 1-9, the leg width is constant and equal to the leg depth at the proximal end of the leg.

As stated above, the body leading and trailing end recess distances 170, 172 are preferably equal to or greater than the local bone cortex thickness. The distances 170, 172 are preferably be in the range of 1-8 mm and may vary for different size implants and different applications.

The leg length 127 is preferably close to the bone thickness along the insertion axis 102. The legs may be the same length or different lengths and they may be staggered at one or both ends. In the illustrative example of FIGS. 1-9, the leg lengths are different and the legs are level at the proximal end but staggered at the distal end. For use in foot surgery, the leg lengths are preferably in the range of 10-50 mm and more preferably in the range of 14-32 mm. For use at other locations, the leg length may be outside of these ranges and can be, for example, quite long in large implants for applications such as tibial osteotomies.

The aperture 118, if present, is sized to receive an appropriate cross fixation fastener. Preferably its length 120 is as long as possible, and corresponds to an angular variation, that gives maximum flexibility for cross fixation placement without colliding with the legs.

The fastener 100 may be provided as a plurality of fasteners having different sizes to accommodate different anatomy. In one example, the fastener is provided as a plurality of fasteners of varying leg length 127 with the leg width 121, depth 123, outboard wall 148, 150 spacing, and divergence angle being the same for each fastener. In this way differing bone thicknesses may be accommodated while using the same instruments described below.

Referring to FIGS. 10-14, a hole forming guide 200 includes a body 202 defining hole axes 204, 206 along which a hole forming tool may be guided. In the illustrative example of FIGS. 10-14, the axes 204, 206 are defined by cylindrical guide holes 208, 210. The guide holes 208, 210 are operable to receive a hole forming tool such as a punch or drill and constrain the hole forming tool to longitudinal motion along the axes 204, 206 to form holes in an underlying bone. The axes 204, 206 are angled to correspond to the divergent legs of the fastener of FIGS. 1-9. The inboard surfaces of the guide holes 208, 210 have a guide hole inboard surface leading end spacing 212 at the leading end 214 of the guide 200 that is equal to or greater than the inboard surface trailing end spacing 165 of the fastener. If the guide hole inboard surface leading end spacing 212 is equal to the fastener leg inboard surface trailing end spacing 165, the inboard surfaces 128, 130 of the fastener legs will just touch the inboard surfaces of the bone holes when the fastener leg trailing ends are inserted flush with the bone surface. Further seating of the fastener legs below the surface of the bone will result in compression of the bone between the fastener legs. Likewise, if the guide hole inboard surface leading end spacing 212 is greater than the fastener leg inboard surface trailing end spacing 165, the inboard surfaces 128, 130 of the fastener legs will just touch the inboard surfaces of the bone holes when the fastener leg trailing ends are proud of the bone surface. Further insertion of the fastener until the trailing ends of the legs are flush with the bone surface will result in compression of the bone. The amount of compression for a given insertion depth of the fastener may be determined by selecting the relationship of guide hole inboard surface leading end spacing 212 to fastener leg inboard surface trailing end spacing 165. With the included angle between the leg inboard surfaces matching the included angle between the hole inboard surfaces, the compression of the bone between the fastener legs is uniform at all positions between the legs normal to the insertion axis and inserting the bone fastener does not create a relative bending moment between the first and second bone portions. The guide 200 further includes a guide slot 216 connecting the holes 208, 210. The slot 216 may be used to guide a chisel, broach, saw or other cutting tool to remove bone and form a connecting slot between bone holes formed using the guide holes 208, 210 for receiving the fastener body 104. Alignment notches 218 are provided to indicate the center of the guide 200. Fixation holes 220 are provided to receive fixation pins or screws to fix the guide in position on a bone.

Referring to FIGS. 15-18, an inserter 300 is configured for use with the fastener 100 of FIGS. 1-9. The inserter 300 includes a body 302 having a distal end 304 and a proximal end 306 including a handle portion 308. The body includes a pair of laterally spaced passages extending from the distal end 304 toward the proximal end 306 and each defining a passage axis 307. The passage axes 307 are angled 309 to align with the cavities 160 in the fastener 100. Side cuts or windows 310 communicate with the passages. Each passage receives a locking bolt 312 in axial sliding and rotating relationship. Each bolt 312 traverses one of the windows 310 exposing the portion of the bolt 312 within the window for manipulation. A knob 314 is fixed to each bolt 312, such as by pinning, to allow a user to rotate the bolt 312 about the passage axis 307 and to serve as a limit to axial travel of the bolt 312 as the knob abuts the proximal or distal margins 316, 318 of the window 310. Each bolt 312 includes a smooth cylindrical portion 320 sized to fit into the trailing portion 162 of the stepped cylindrical cavity 160 in one of the fastener legs. Each bolt 312 includes a threaded portion 322, distal to the smooth portion 320, sized to screw into the threaded leading portion 164 of the stepped cavity 160. The proximal end 306 of the inserter 300 includes an engagement portion configured to rotationally couple to a cross fixation guide discussed further below. In the illustrative example of FIGS. 15-18, the engagement portion includes a socket 324 extending distally into a top surface 325 of the handle portion 308 and a peripheral edge 326.

Figure 18:
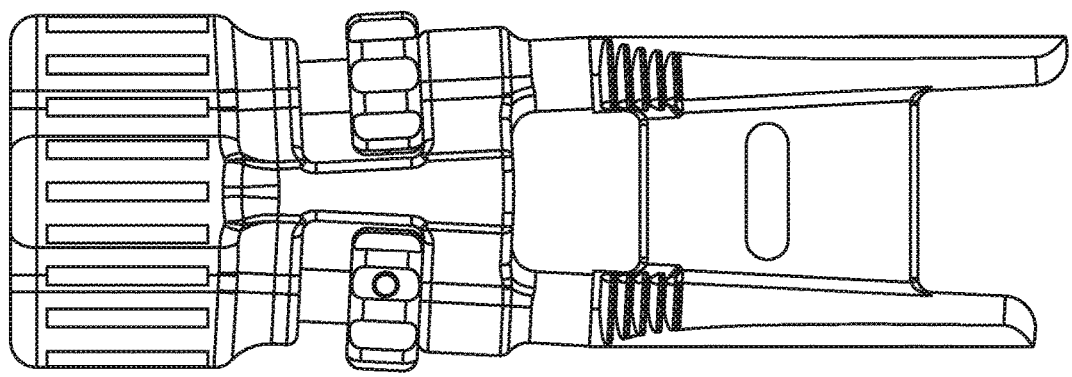
FIGS. 17 and 18 are front elevation views of the inserter of FIG. 15 with the implant of FIG. 1.
Figure 17:
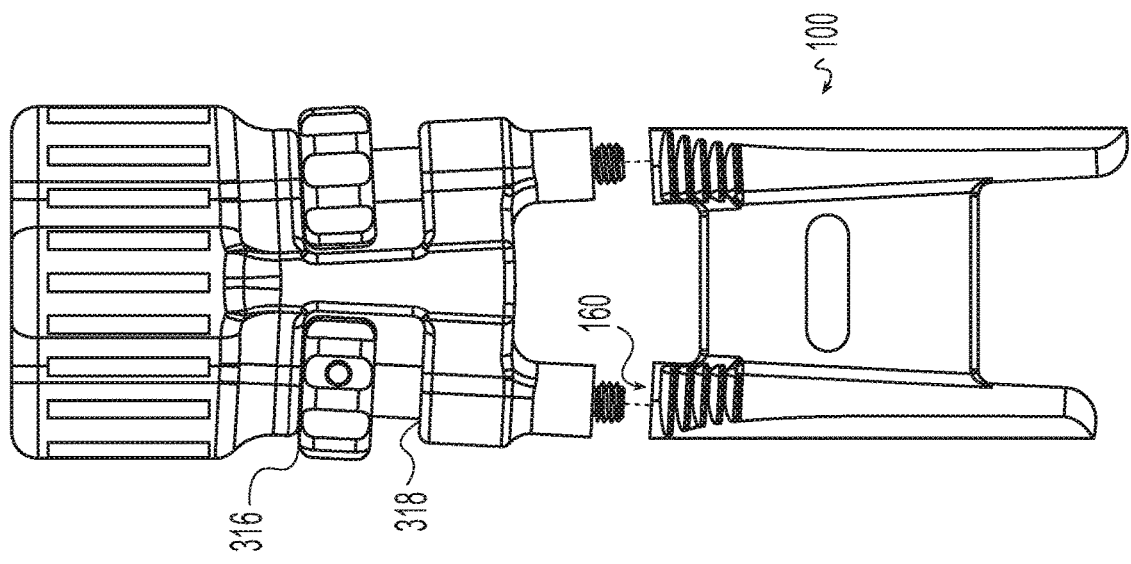
Figure 16:
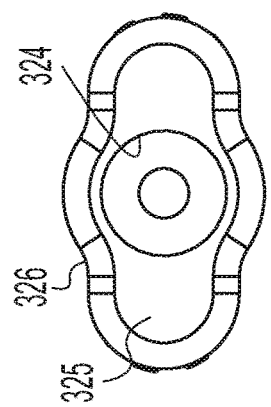
FIG. 16 is a top view of the inserter of FIG. 15.
Figure 15:
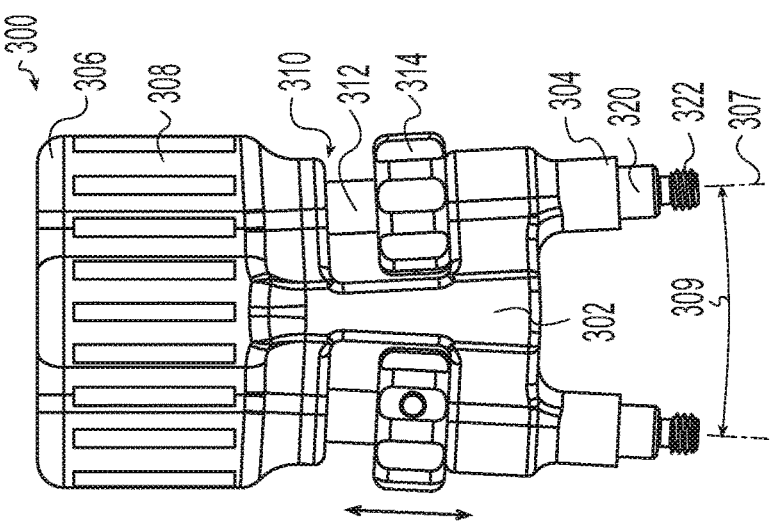
FIG. 15 is a front elevation view of an example of an inserter for the bone implant of FIG. 1.
Figure 19:
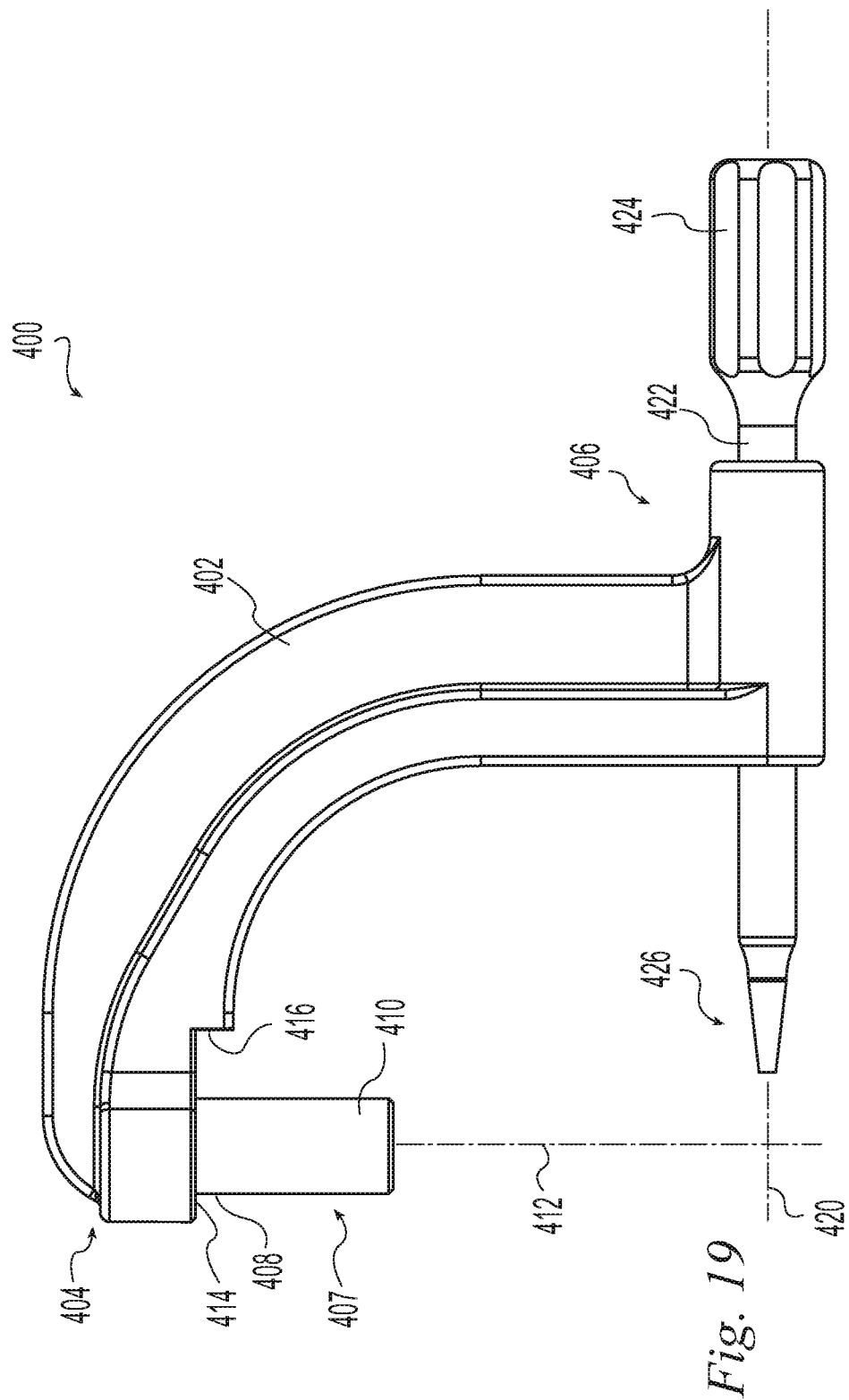
FIG. 19 is a front elevation view of an example of a fixation guide for the bone implant of FIG. 1.

The inserter 300 is joined to the fastener 100 by first sliding the locking bolts 312 proximally until the knobs 314 abut the proximal margin 316 of the window 310 as shown in FIG. 17. The threaded portion 322 may then be inserted into the cavity 160 of the fastener 100. Each knob 314 is then rotated to thread the locking bolt 312 into the cavity 160 and secure the fastener 100 to the inserter 300 as shown in FIG. 18.

Figure 20:
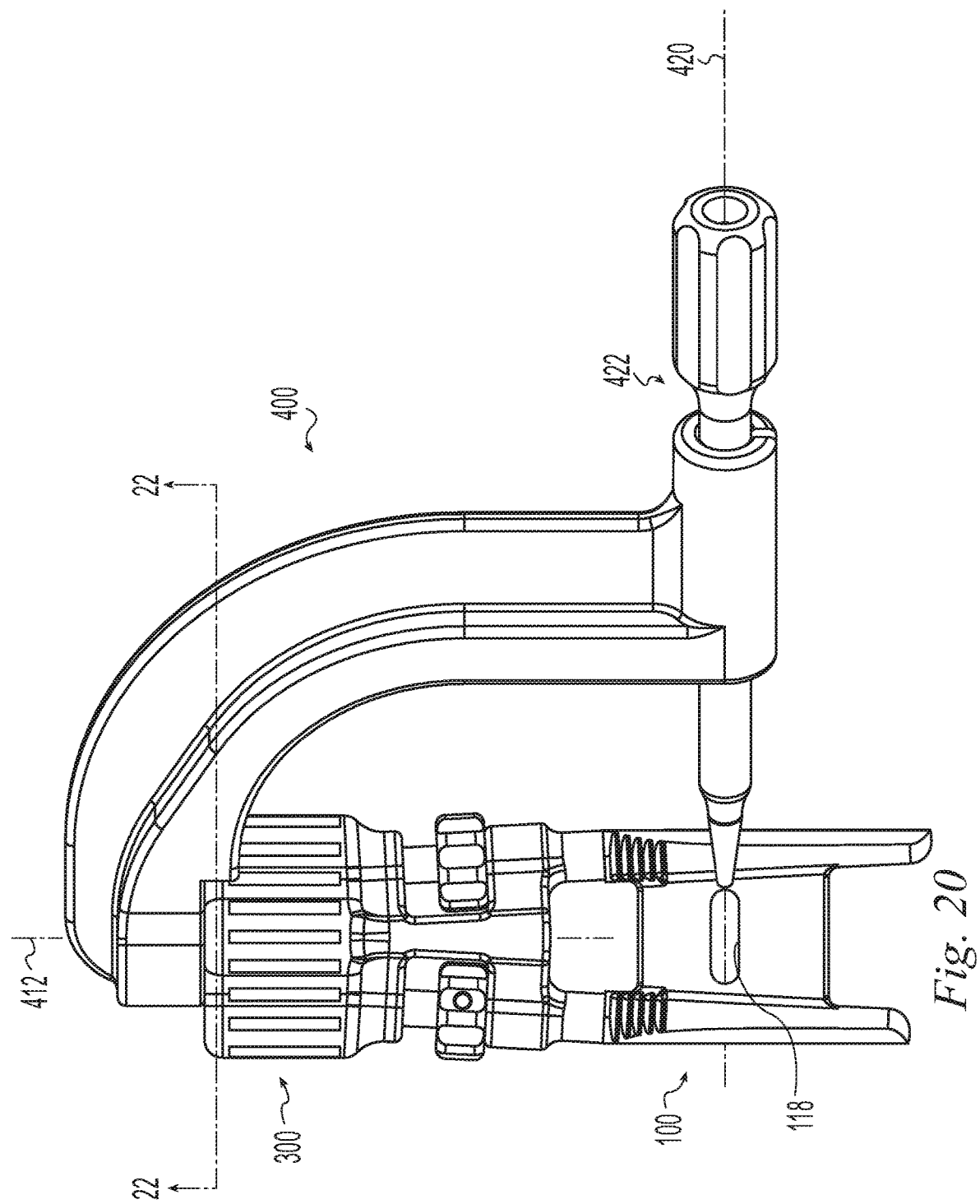
FIG. 20 is a perspective view of the fixation guide of FIG. 19 with the inserter of FIG. 15 and the implant of FIG. 1.

Referring to FIGS. 19-22, a cross fixation guide 400 is engageable with the inserter to guide placement of an elongate member through the aperture 118 of the fastener 100. The elongate member may be a pin, screw, drill, wire or other member. For example, the guide 400 may be used to place a guide wire through the aperture and the guide wire may be used to insert a cannulated screw. The cross fixation guide 400 includes an arcuate guide body 402 having at one end an engagement portion 404 and at an opposite end a guide portion 406. The engagement portion 404 is configured to rotationally couple to the inserter 300. In the illustrative example of FIGS. 19-22, the engagement portion 404 includes a stud 407 extending distally from the guide body 402 from a proximal end 408 to a distal end 410 and defining an engagement axis 412. The guide 400 includes an axial stop and a rotational stop to aid in positioning the guide 400 relative to the inserter 300. In the illustrative example of FIGS. 19-22, a shoulder 414 formed near the proximal end 408 of the stud 407 serves as the axial stop and a side surface 416 transverse to the shoulder 414 and formed on the guide body 402 serves as the rotational stop. The guide portion 406 defines a cross fixation insertion axis 420 transverse to the engagement axis 412 and along which a fixation member may be guided to pass through the fastener aperture 118. In the illustrative example of FIGS. 19-22, the guide portion includes a passage through the guide body 402 defining the cross fixation insertion axis 420 and a sleeve 422 received in the passage in axial sliding relationship. The sleeve 422 includes an axial through passage, proximal handle portion 424 and a distal leading end 426 forming a tapered tip. The axial through passage is sized to guide a guide wire along the cross fixation insertion axis 420. The sleeve may be translated along the axis 420 relative to the guide body 402 to position the leading end 426 at a desired spacing from a bone. The cross fixation guide 400 is coupled to the inserter 300 by inserting the stud 407 into the socket 324 until the shoulder 414 abuts the top surface 325 of the inserter handle 308 as shown in FIG. 20. Thus assembled, the cross fixation insertion axis 420 is aligned with the center of the fastener aperture 118. The cross fixation guide 400 may be rotated relative to the inserter 300 about the engagement axis 412 through an infinite number of angular positions between a first angular position shown in solid line in FIGS. 21 and 22 and a second angular position shown in dashed lines. Preferably, the guide and inserter define stops between them limiting the angular positions. For example, a fixation member to be inserted through the fastener aperture 118, such as screw 636 in FIG. 36, has a longitudinal axis and a transverse dimension normal to the longitudinal axis. The fixation member may be inserted through the aperture 118 at an included angle between the longitudinal axis of the fixation member and the aperture length axis ranging from 90 degrees to a value corresponding to a projected length of the aperture along the fixation member longitudinal axis equal to or greater than the fixation member transverse dimension. Preferably, the angular stops limit the rotation of the guide to be within this range so it is guaranteed that the fixation member will fit through the aperture. In the illustrative example of FIGS. 19-22 the first and second angular positions are limited by abutment of the side surface 416 of the cross fixation guide with the peripheral edge 326 of the inserter 300.

Figure 25:
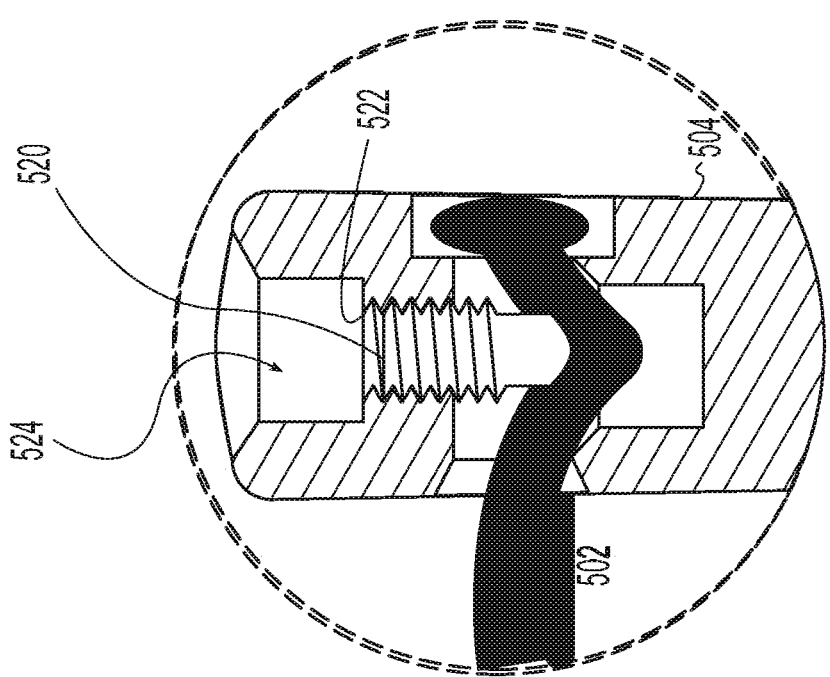
FIG. 25 is a detail view of the bone implant of FIG. 25.
Figure 24:
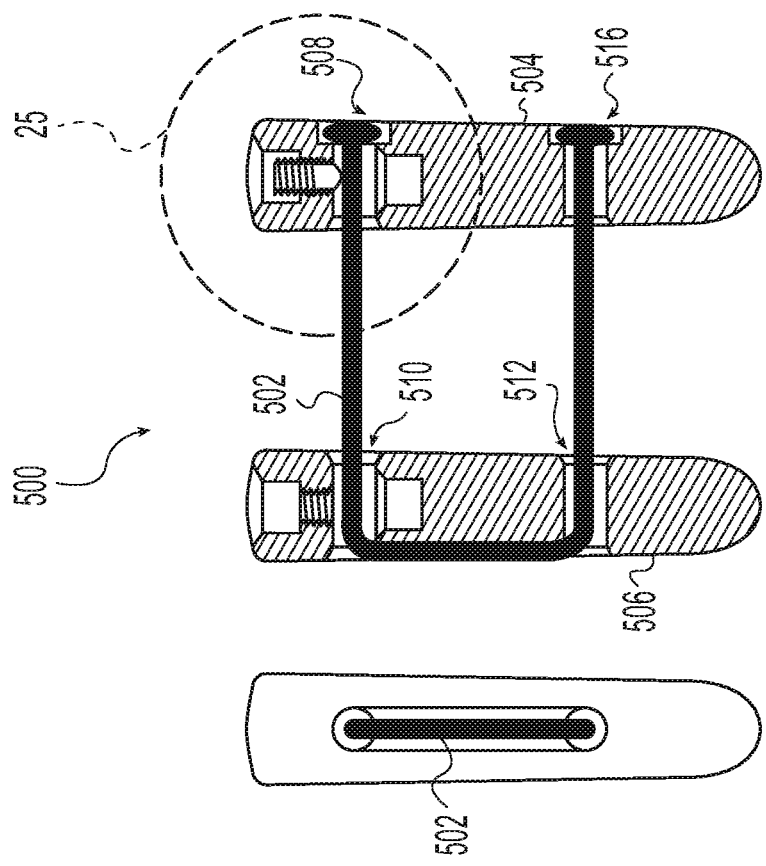
FIG. 24 is a front elevation view of the bone implant of FIG. 23.
Figure 23:
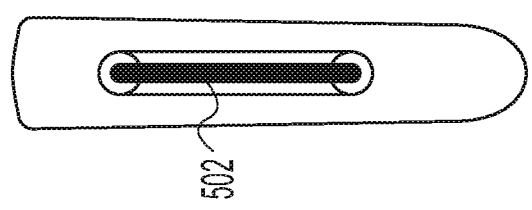
FIG. 23 is a side elevation view of an alternative example of the bone implant of FIG. 1.

FIGS. 23-25 depict another illustrative example of a fastener 500 according to one example of the invention in which the rigid body 104 of fastener 100 has been replaced with a flexible member 502. The fastener includes first and second legs 504, 506. The flexible member 502 connects to axially spaced first and second connectors on the first leg 504 and passes through a receiver on the second leg 506 in sliding relationship to permit the angle between the fastener legs to be varied between arbitrary angles and to facilitate equal tensioning of the flexible member 502. In the illustrative example of FIGS. 23-25, the flexible member 502 is attached at a first location 508 on the first leg 504, extends to the second leg 506, passes through a first passage 510 in the second leg, extends axially along a portion of the second leg, passes through a second passage 512 in the second leg, and returns to the first leg 504 where it is attached at a second location 516. The flexible member 502 is able to slide freely within the passages 510, 512 in the second leg to allow the fastener legs 504, 506 to be variably angled relative to one another and so that tension in the flexible member is distributed equally throughout the flexible member 502. The fastener 500 may include a tensioning device operable to shorten the portion of the flexible member 502 that extends outwardly from the first leg 504. In the illustrative example of FIGS. 23-25, the first leg 504 includes a tensioning member operable to shorten the flexible member, such as for example by pressing the flexible member into the socket 524. For example, a tensioning screw 520 may be engaged with the threaded portion 522 of the socket 524. The flexible member 502 is attached to the first leg 504 so that it passes through the threaded portion 522 distal to the tensioning screw 520. Advancing the tensioning screw 520 presses the flexible member distally into the socket causing a portion of the flexible member 502 to be pulled into the first leg 504 and thus shortening the portion of the flexible member 502 that extends outwardly from the first leg 504.

In use, for example, holes may be formed in the bone using a hole guide as in the preceding examples. The legs 504, 506 may be attached to a driver, for example like that of FIG. 15, and inserted into the bone holes. Tensioning screw 520 may then be inserted and advanced to shorten the flexible member and compress the bone.

Figure 26:
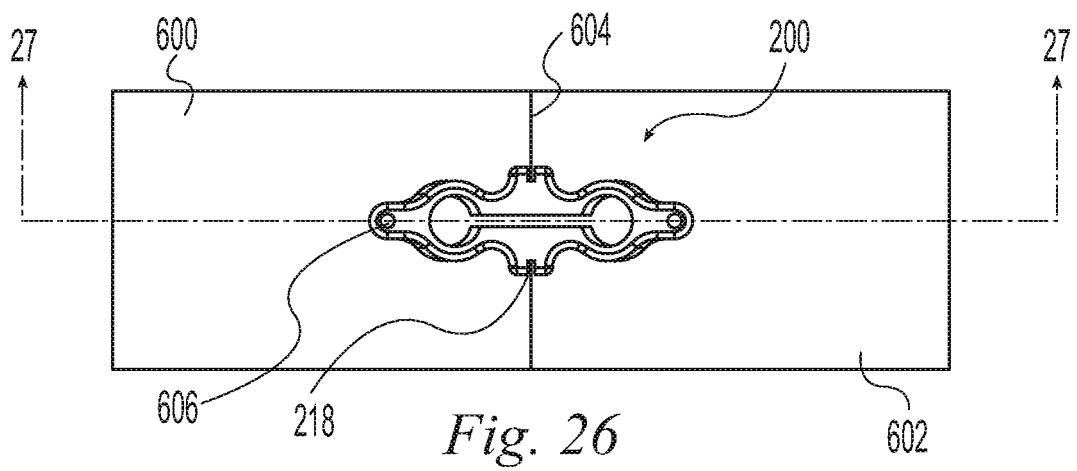
FIGS. 26-37 illustrate an example of a surgical method utilizing the implant of FIG. 1.

FIGS. 26-37 illustrate a method of using the fastener and instruments of FIGS. 1-22. Referring to FIG. 26, first and second bone portions 600, 602 abut at an interface 604 such as a joint articular surface, fracture, osteotomy cut plane, or other interface. The hole forming guide 200 is positioned over the bone portions with the alignment notches 218 aligned with the interface 604 to center the guide 200 over the interface 604. Fixation pins 606 may be placed in holes 220 in the guide 200 to secure the guide 200 to the bone portions.

Figure 27:
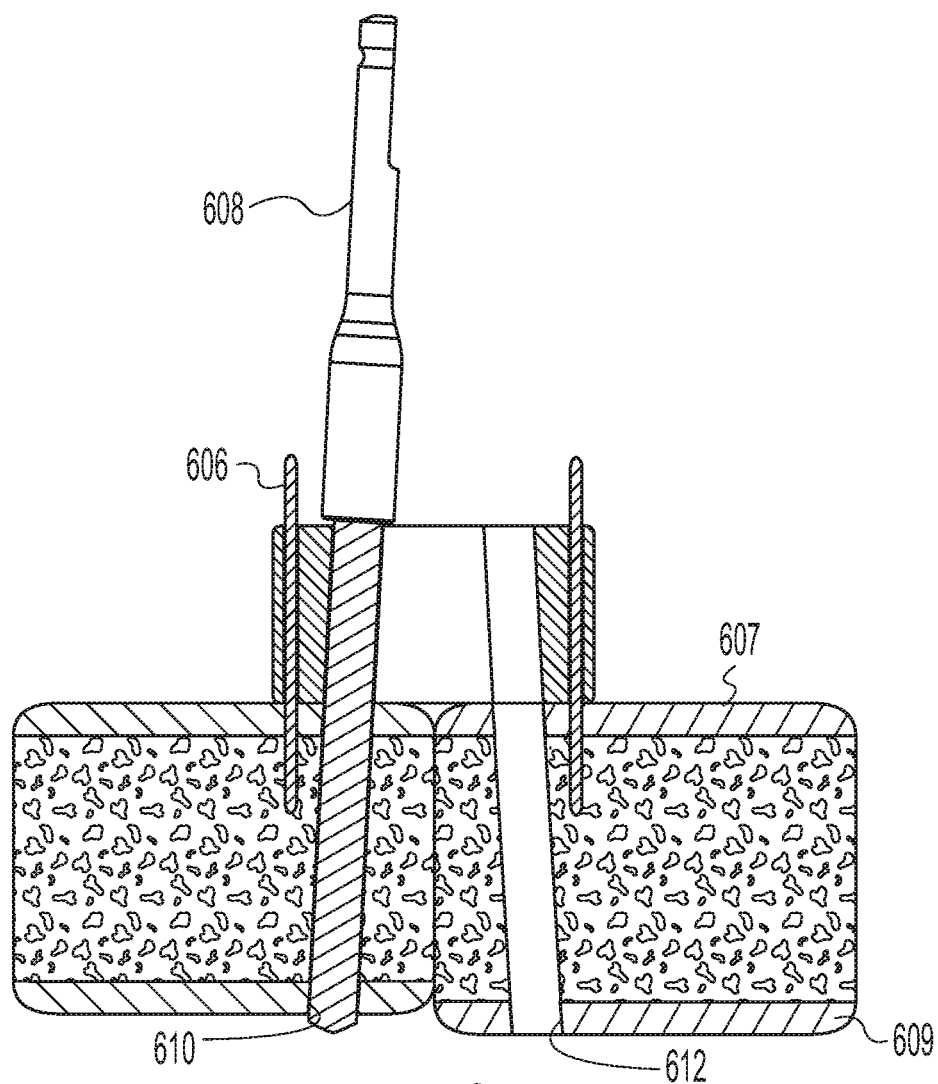

Referring to FIG. 27, a drill 608 is guided in the guide holes 208, 210 to form corresponding holes 610, 612 in the bone. Preferably these holes pass through the bones so that the legs of the fastener 100 will engage the bone portions bi-cortically at the proximal and distal cortices 607, 609.

Figure 28:
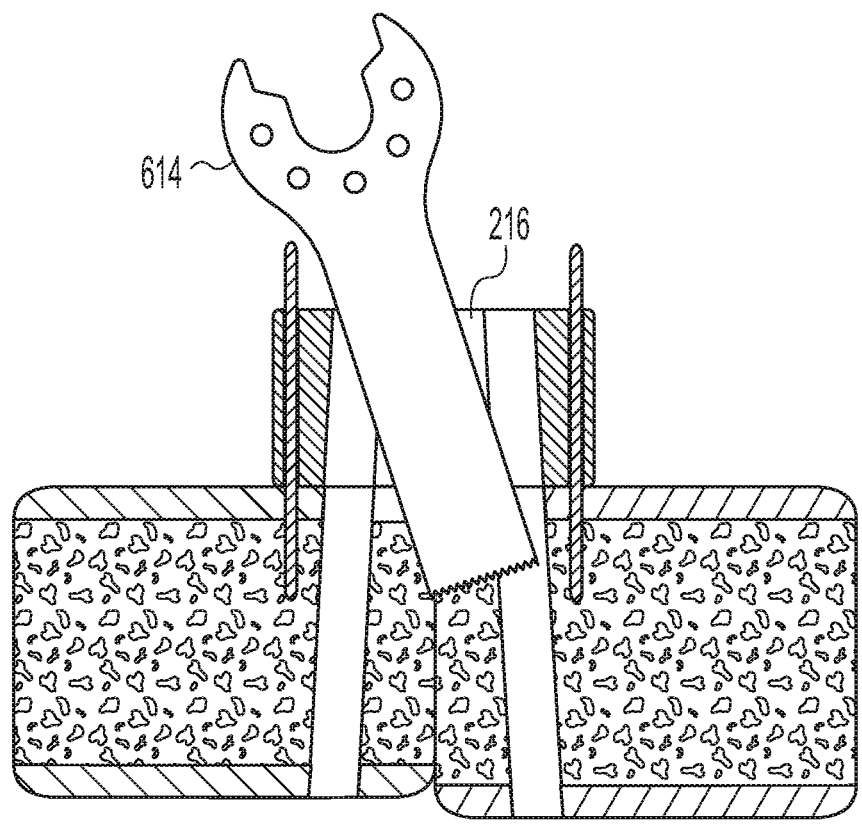
Figure 29:
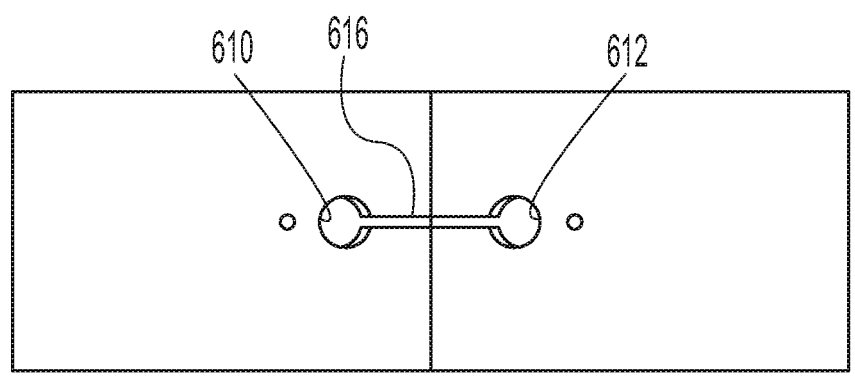

Referring to FIGS. 28 and 29, a saw blade 614 is guided in the saw slot 216 of the guide 200 to form a bone slot 616 to ease insertion of the fastener body through the proximal cortex. Preferably the saw slot only extends through the proximal bone cortex since only a proximal slot s needed to insert the fastener body.

Figure 30:
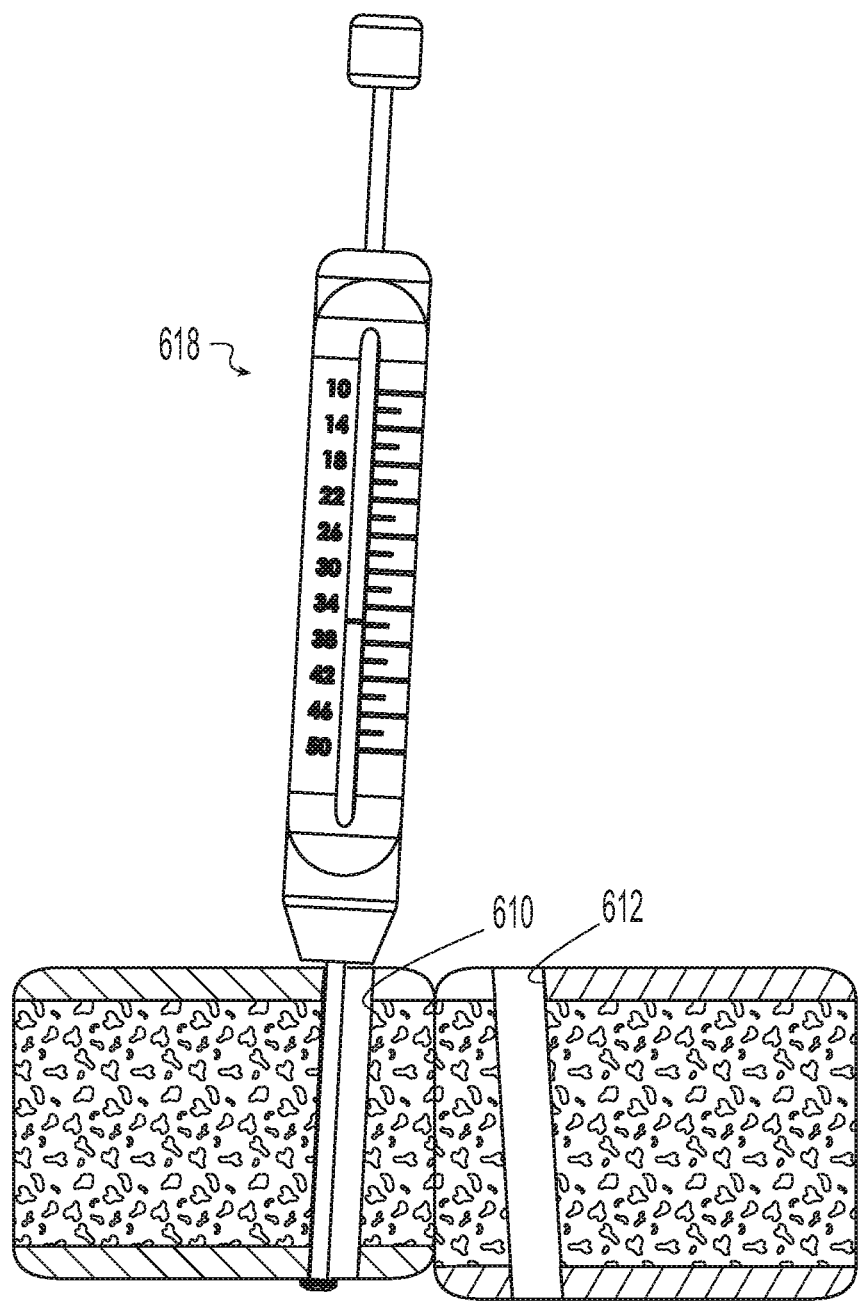

Referring to FIG. 30, a depth gauge 618 is used to probe the bone holes 610, 612 to determine their depth as an aid in selecting a fastener of the appropriate size to provide bi-cortical fixation. Depending on the shape of the bone portions, the holes may have different depths and may preferably receive a fastener having different length legs.

Figure 31:
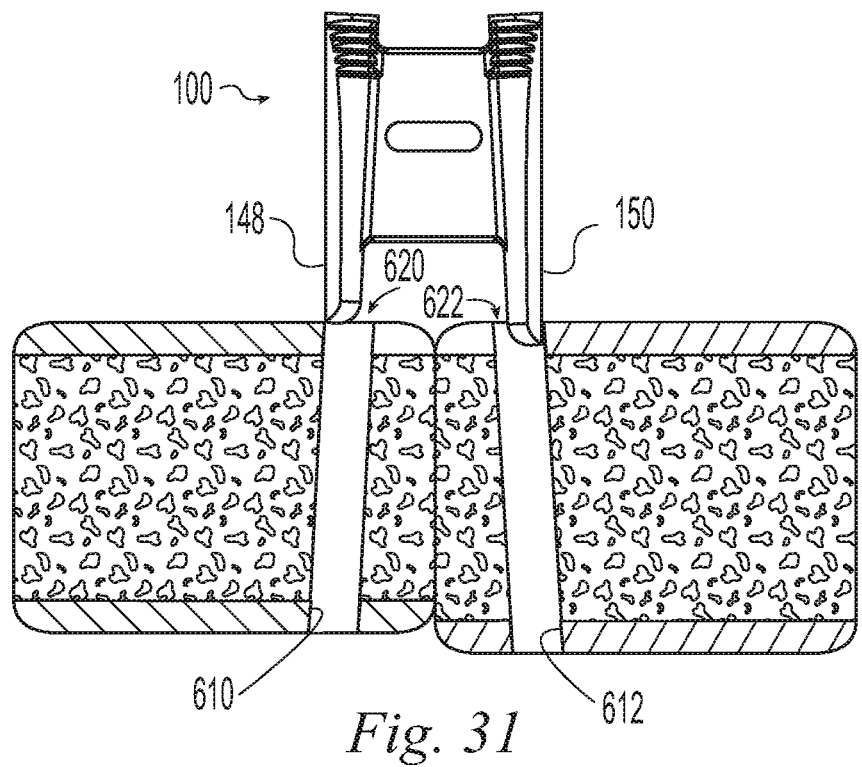
Figure 32:
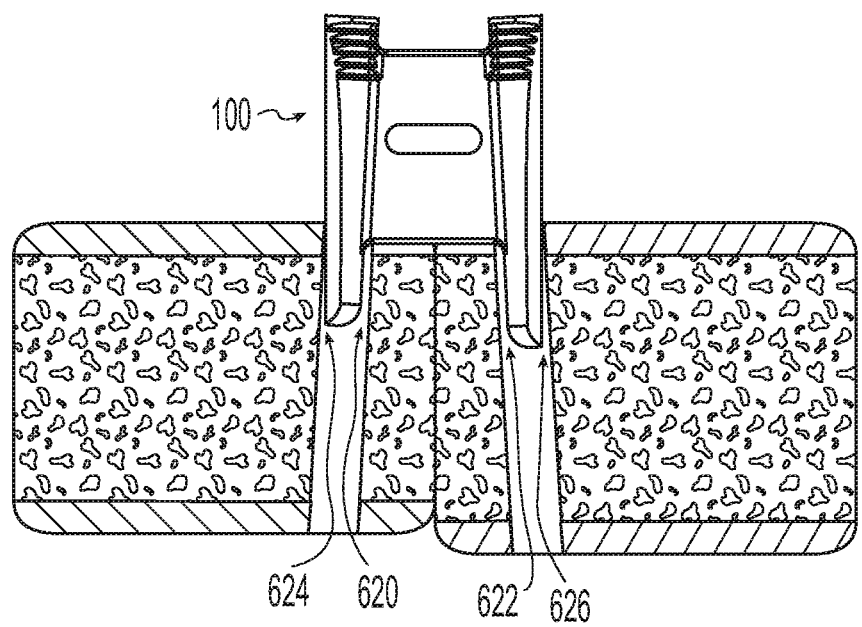

Referring to FIGS. 31 and 32, a fastener 100 is started into the bone holes 610, 612. The inserter 300 has been omitted from the figures to simplify the drawings. The outboard surfaces 148, 150 of the fastener legs are sized to match the proximal spacing of the outboard bone hole walls. Since outboard surfaces 148, 150 are parallel, they stay in contact with the proximal portion of the bone holes 610, 612 as the fastener is advanced into the bone portions. Inboard gaps 620, 622 are present between the fastener legs and the bone holes. Outboard gaps 624, 626 occur between the fastener legs and the bone holes distal of the proximal edge of the bone holes as the fastener is advanced.

Figure 33:
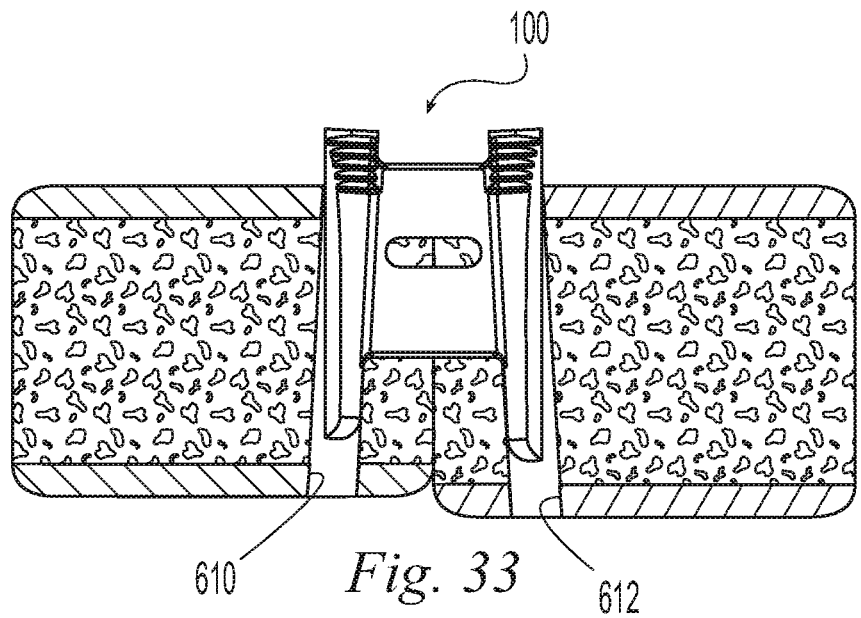
Figure 34:
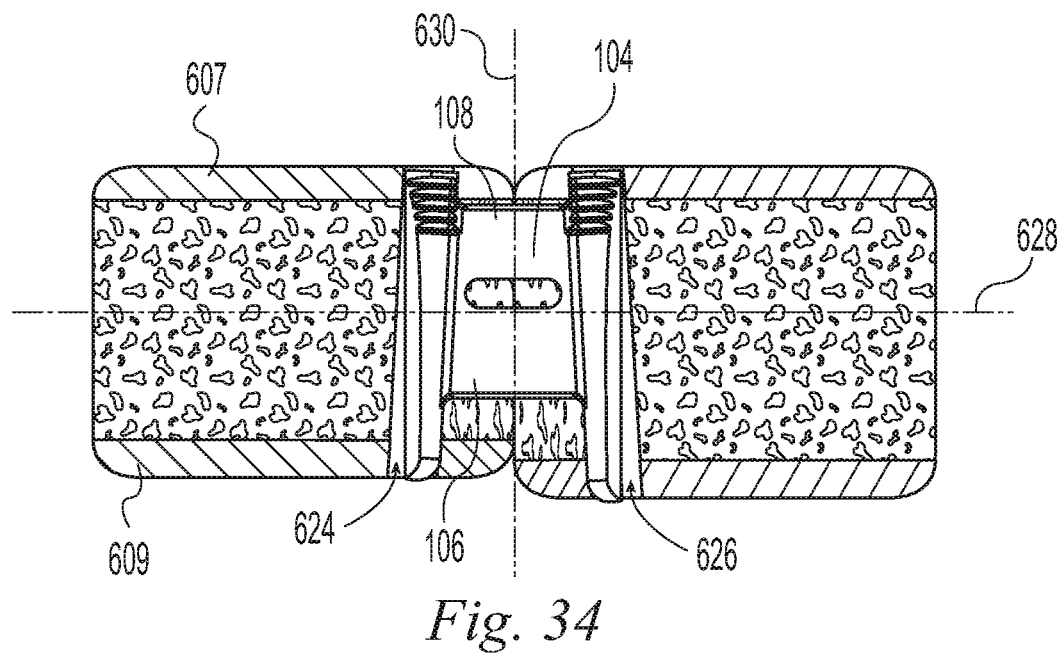

Referring to FIGS. 33 and 34, the inboard gaps 620, 622 diminish as the fastener is advanced until at some point in the fastener's travel, the fastener leg inboard surfaces 128, 130 contact the inboard bone hole walls. Since the inboard surfaces 128, 130 diverge at the same angle as the bone holes 610, 612, the fastener leg inboard surfaces 128, 130 contact the bone all along the length of the portions of the legs that have been inserted. Further advancing the fastener will compress the bone between the fastener legs uniformly along the fastener legs proximally to distally. In other words, as the fastener is further advanced, the bone is compressed between the fastener legs normal to the insertion direction the same amount at every point along the fastener legs proximally to distally. For bones having a longitudinal axis 628 normal to the insertion direction 630, the bone portions will be compressed axially relative to the longitudinal axis 628. The amount of compression can be tailored by setting the spacing of the inboard surfaces of the bone holes 610, 612 relative to the fastener leg inboard surfaces 128, 130. With the inboard bone hole surfaces further apart, the inboard fastener surfaces will contact the bone holes earlier in the fastener's travel and further advancing the fastener to a final resting position will cause relatively more compression. Alternatively, with the inboard bone hole surfaces closer together, the inboard leg surfaces will contact the bone holes later in the fastener's travel and further advancing the fastener to the same final resting position will cause relatively less compression. Preferably the fastener 100 is seated with the trailing ends of the fastener legs flush with or below the bone surface to reduce irritation of surrounding tissues. Preferably the fastener 100 is seated with the trailing end 108 of the body below flush and more preferably below the proximal cortex 607 to allow for cortical healing above the fastener body 104. To remove the fastener, it is pulled proximally. The sharpened trailing edge of the body 104 aids in passing the body through any bone that has grown over the body 104. Preferably the leading end 106 of the body stays inside the bone and more preferably the leading end 106 is above the distal cortex 609 to preserve bone strength.

Figure 35:
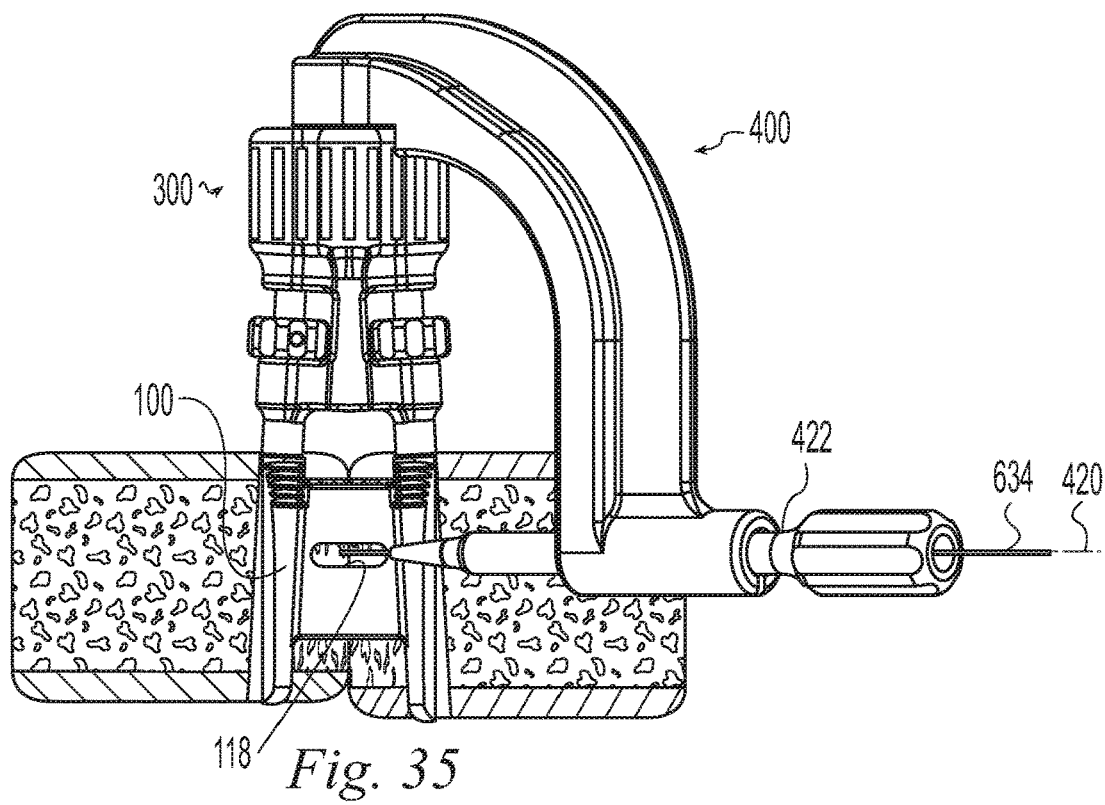
Figure 36:
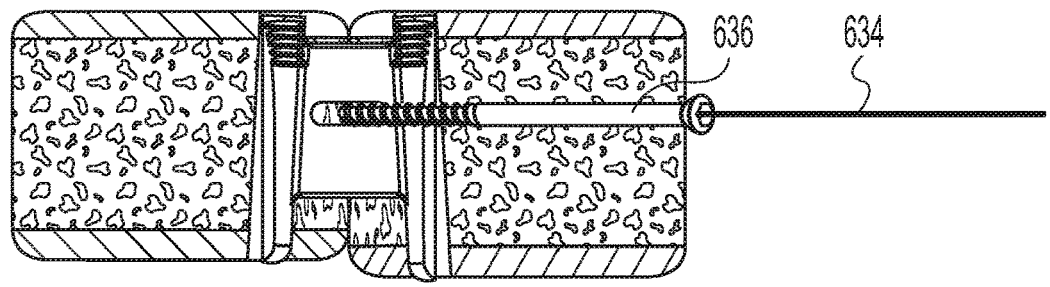
Figure 37:
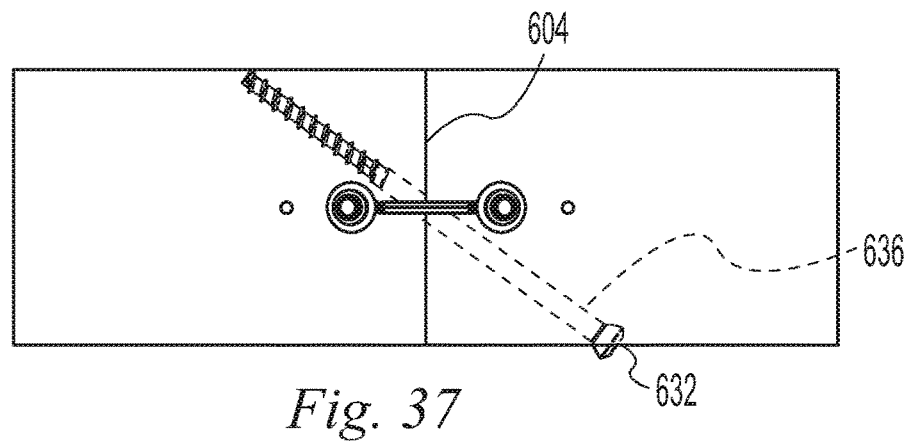

Referring to FIGS. 35-37, the cross fixation guide 400 is mounted to the inserter 300 which is attached to the fastener 100. The cross fixation guide 400 is pivoted relative to the inserter 300 to direct the cross fixation axis 420 in a desired direction. For example, it may be pivoted to align with a desired entry point on the bone 632. The rotation stops guarantee that the axis 420 is not angled so acutely as to prevent passage of a fixation member through the fastener aperture 118. The sleeve 422 is translated axially to position the sleeve close to the bone entry point 632 to stabilize a guide wire 634 as it is inserted through the sleeve, into the bone, and through the aperture 118. A fixation screw 636 is advanced over the guide wire 634 into the bone and through the aperture 118. The guide wire 634 is then removed. Preferably the screw 636 is sized and positioned for bi-cortical fixation. Preferably the screw passes through both bone portions to further stabilize the interface 604.

The implants, instruments and methods of examples of the invention may be used at many different locations within a patient to secure bone portions relative to one another and may further be used to form various constructs as shown in the illustrative examples of FIGS. 38-44. While illustrative, these examples are not comprehensive and it will be apparent to one skilled in the art that these implants, instruments, and methods may be used anywhere two bone portions are to be secured. The size and proportion of the fastener may be varied to suit a particular anatomical location.

Figure 38:
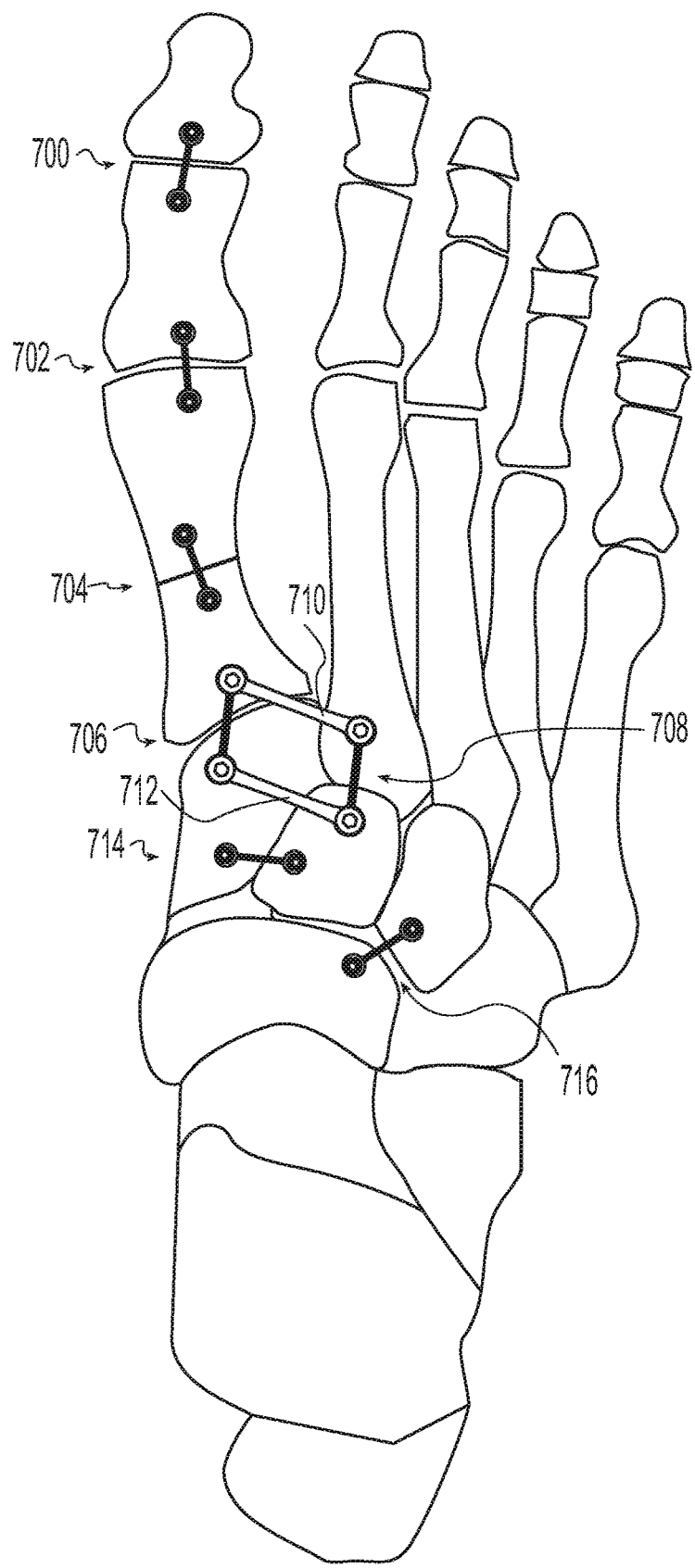
FIGS. 38-44 illustrate examples of surgical applications for the implant of FIG. 1.

Referring to FIG. 38, a human foot illustrates various examples of applications for the invention. A phalangeal fusion is indicated at 700. A metatarsophalangeal fusion is indicated at 702. A fusion of a midshaft fracture or osteotomy is indicated at 704. Metatarsocuneiform fusions are indicated at 706 and 708. In this example, joining elements 710, 712 have been attached between separate fasteners to form a construct in a lisfranc procedure. For example, the joining elements 710, 712 may be attached with screws threaded into the sockets in the proximal ends of the fastener legs. The joining elements 710, 712 may be rigid or flexible depending on the amount of constraint desired. Tarsal fusions are indicated at 714 and 716.

Figure 39:
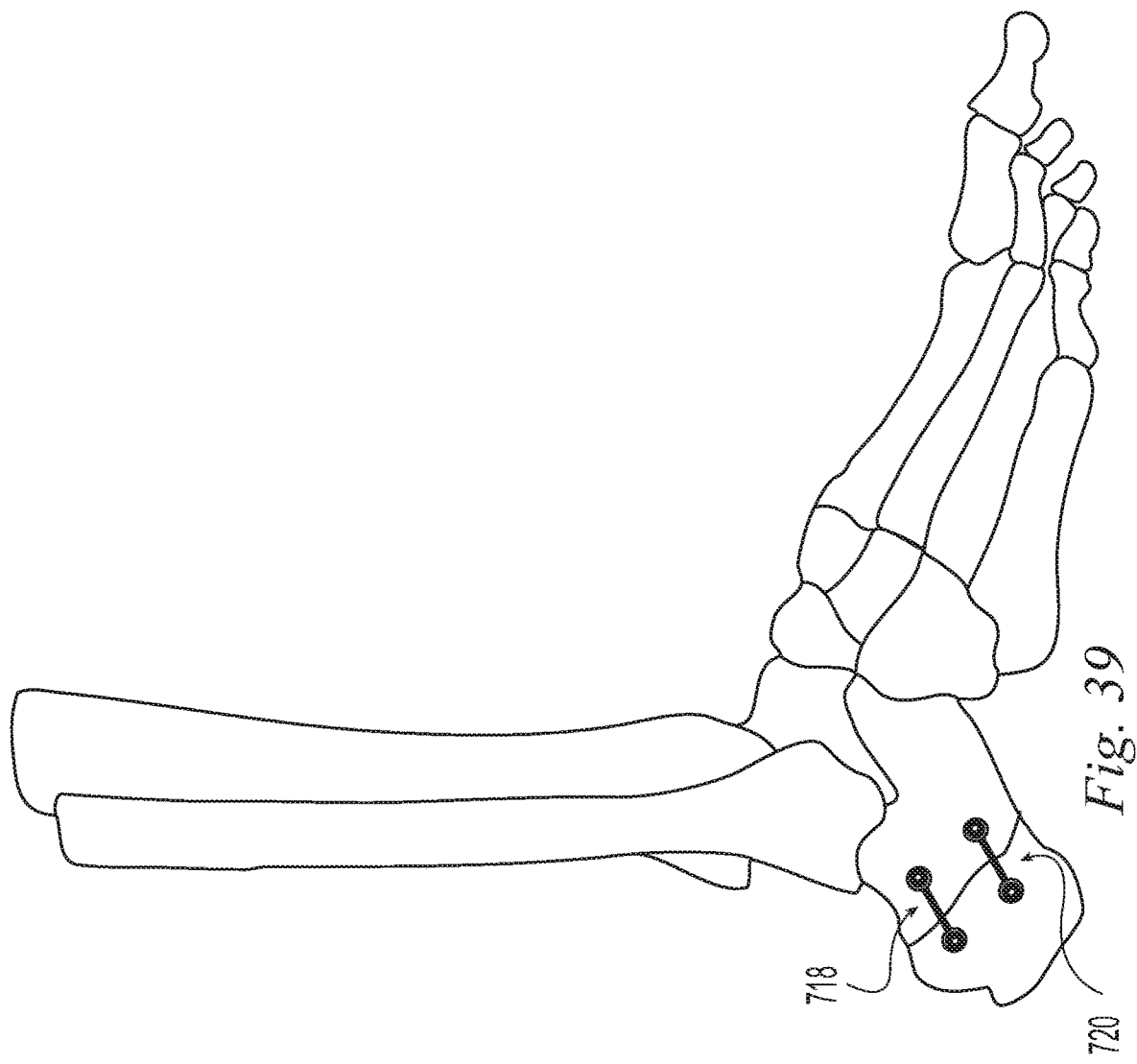

Referring to FIG. 39, a calcaneal osteotomy has been fixed using fasteners according to one example of the invention at 718 and 720.

Figure 40:
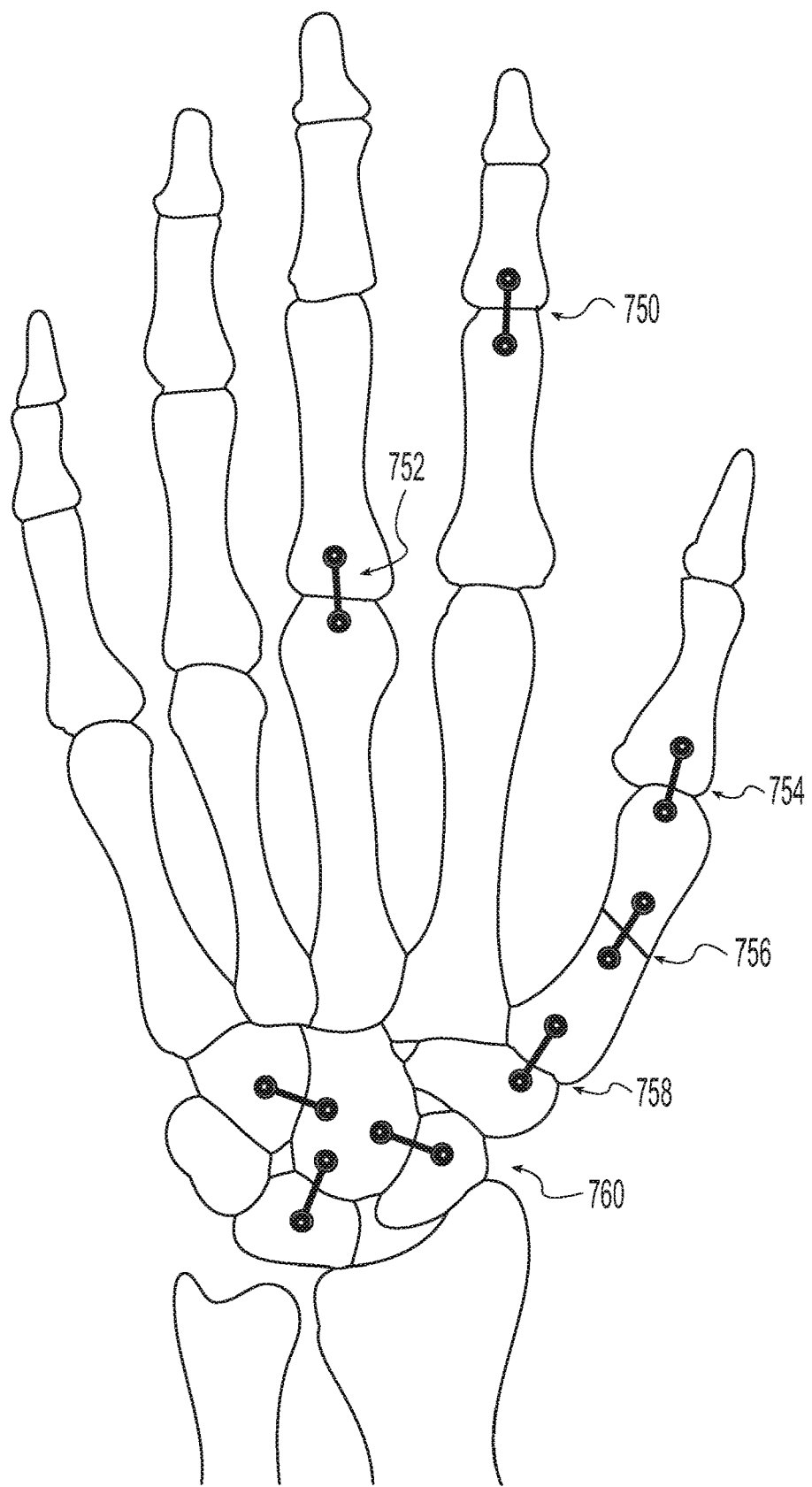

Referring to FIG. 40, applications in the human hand are illustrated similar to those shown for the foot. For example, these may include phalangeal fusion 750, metacarpophalangeal fusion 752 and 754, midshaft fusion 756, metacarpocarpal fusion 758, and carpal fusion 760.

Figure 42:
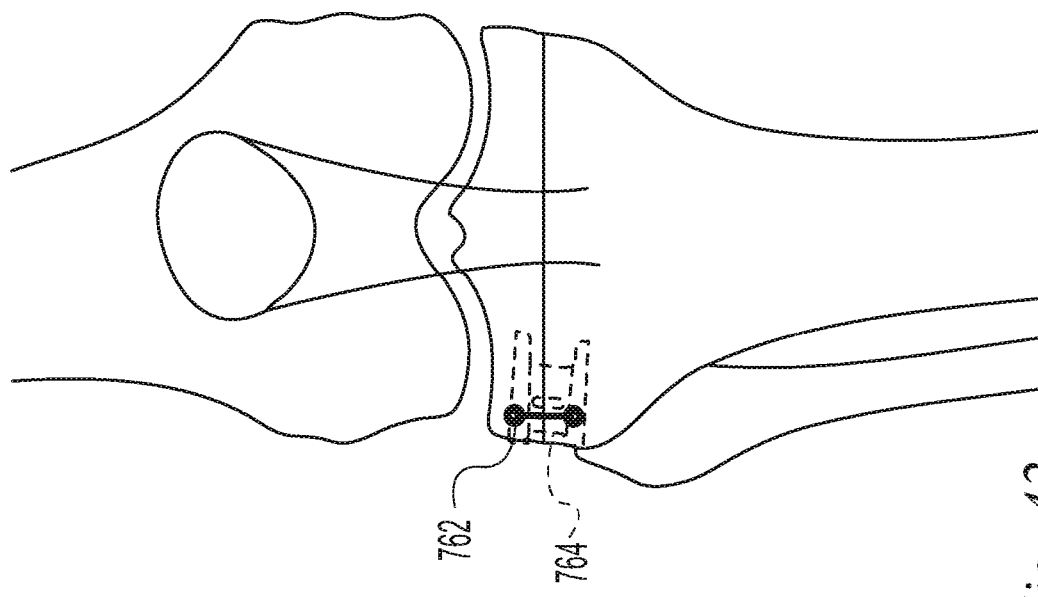
Figure 41:
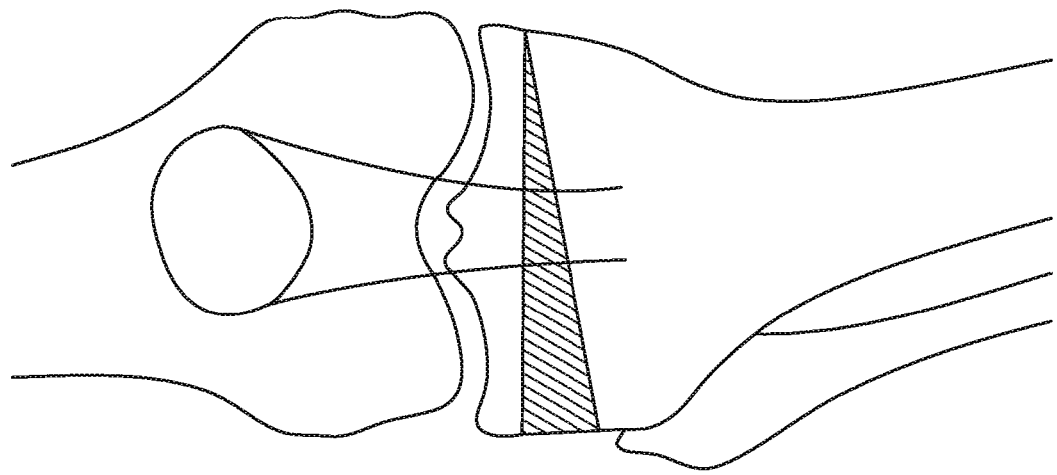

Referring to FIGS. 41 and 42, a closing wedge tibial osteotomy is illustrated in which the closed wedge is fixed with one or more of an anteriorly 762 and/or laterally 764 placed fastener according to one example of the invention.

Figure 44:
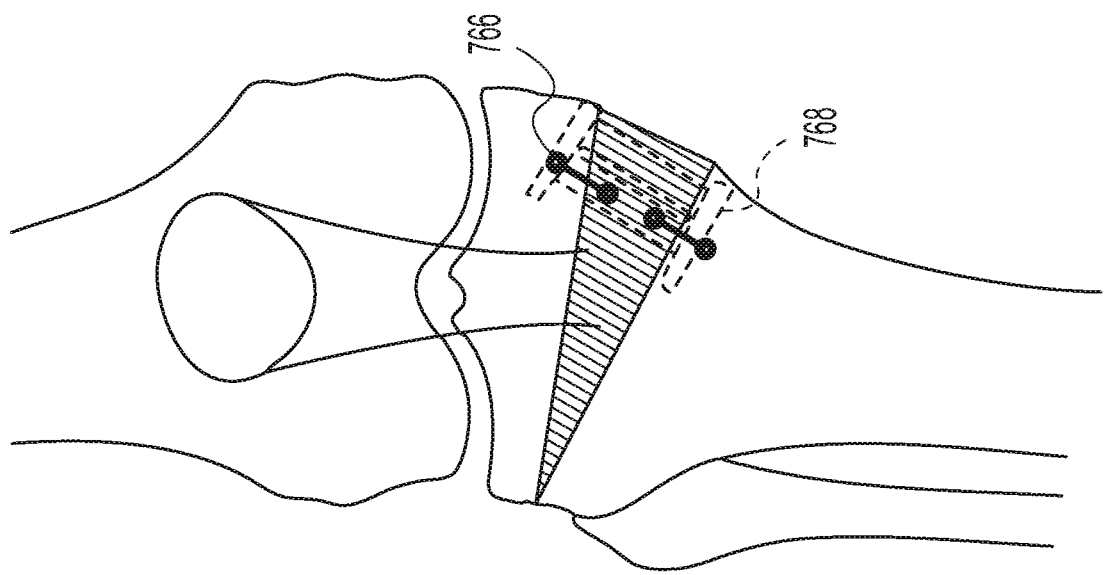
Figure 43:
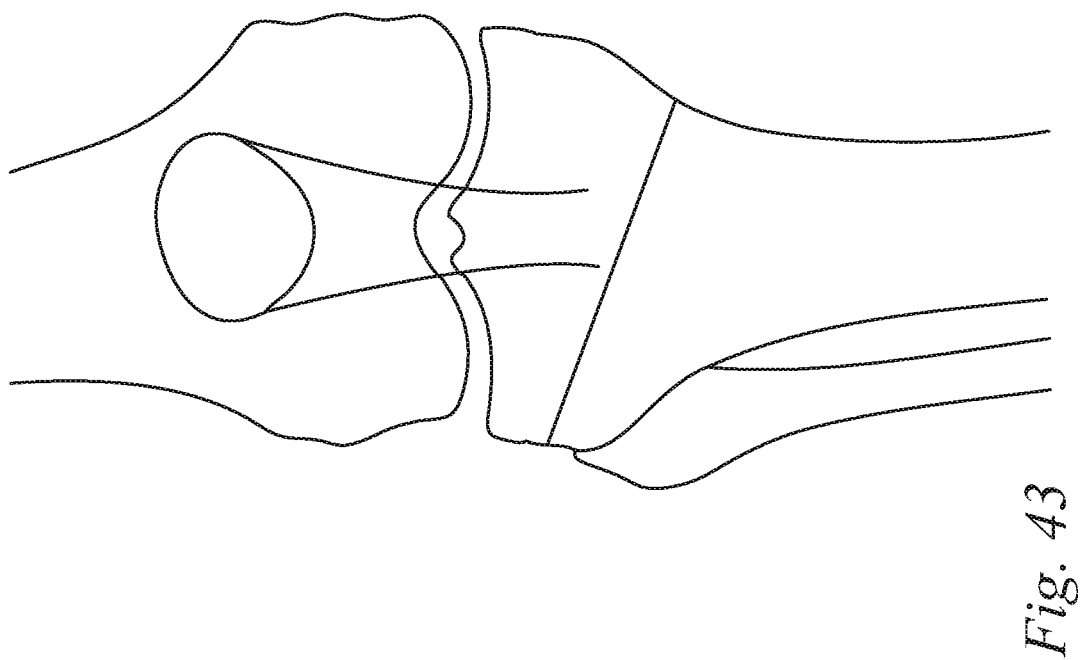

Referring to FIGS. 43 and 44, an opening wedge tibial osteotomy is illustrated in which a graft is fixed into the opened wedge with one or more of an anteriorly 766 and/or medially 768 placed fastener according to one example of the invention. For illustration purposes, the medial fastener 768 is proportioned so that the fastener legs are inserted into tibial bone on either side of the graft.

In addition to securing two bone portions, it may be desirable to secure a spacer such as an articulating surface or fusion implant to a bone. For example, it is common practice to replace one or more of the articular surfaces of a diseased or injured skeletal joint to restore anatomic motion and/or reduce pain. Such joint replacement procedures may replace for example a discrete diseased portion of the joint as in a resurfacing procedure or in a uni-compartmental arthroplasty procedure. Joint replacement procedures may replace the entire articulating surface of one bone of a joint leaving the other bone, or bones, in their natural state such as for example in a hemi-arthroplasty procedure. Joint replacement procedures may replace all of the articulating surfaces at a joint as in, for example, a total joint arthroplasty. Often the implants utilized include a spacer having a base plate and/or a stem to anchor the implant to the underlying bone and may include surfaces for cementitious or osseous integration for enhanced fixation. Joint arthroplasty has been proposed for use at the shoulder, elbow, wrist, hand, and finger joints of the upper extremity. It has likewise been proposed for use at the hip, knee, ankle, foot, and toe joints of the lower extremity. Joint arthroplasty has been proposed for use between adjacent vertebrae of the spine. Joint implants may include articulating spacers to facilitate motion between bones or they may include stationary spacers intended to cause joint fusion with a desired bone spacing. FIGS. 45-50 illustrate an example of an implant 800 for resurfacing at least a portion of an articulating end of a bone adjacent a skeletal joint in one example of the invention. The form of the articular surface of the implant may take any form suitable for a particular joint in the body.

In the example of FIGS. 1A-9, features of the implant inserted into opposing bone portions cause compression of one bone portion against another bone portion. In the example of FIGS. 45-57, features of the implant cause compression of a portion of the implant against an external surface of a bone such as a natural or prepared surface. For example, a first portion of the implant contacts an external surface of the bone and a second portion of the implant is inserted into the bone to cause compression of the first portion of the implant against the external surface of the bone. These features may be incorporated in an implant suitable for any skeletal joint.

By way of example, FIGS. 45-50 illustrate an implant 800 in the form of a tibial prosthesis that provides an articular surface on the proximal end of a tibia after it has been prepared by removing the natural articular surface to create a planar surface. The implant 800 includes a spacer or articular portion that is positioned on a surface of a prepared tibia and an anchor portion including a leg that is inserted into the tibial bone. The implant includes an insertion axis 802 extending between a leading end 804 and a trailing end 806. In the illustrative example of FIGS. 45-50, the articular portion comprises a separate bearing component 810 and a tray component 812 removably joined together. Alternatively, the bearing component and tray component may be a single unitary construct. The bearing component 810 has an upper bearing surface 814 for articulation with an opposing bone or implant component (not shown). The tray component 812 has a lower bone engaging surface 816 that rests on the surface of the prepared tibia. In the example of FIGS. 45-50, the lower surface 816 is planar and parallel to the insertion axis. The lower face 816 may include various bone ingrowth or cement bonding features as are known in the art. The lower surface 816 may include roughened textures, spikes, tabs, posts, and/or other features for immediate mechanical engagement of the bone surface.

A leg 822 is joined to the lower bone engaging surface of the spacer for insertion into the tibia. In the illustrative example of FIGS. 45-50, the leg is joined to the spacer by way of an intermediate body 820. The anchor portion includes the body 820 joined to and extending from the lower surface 816 and the leg 822 joined to the distal end of the body 820. In the illustrative example of FIGS. 45-50, the body 820 and leg 822 are configured generally as shown and described relative to the example of FIGS. 1A-9 with the second leg of FIGS. 1A-9 being replaced by the spacer. As with the example of FIGS. 1A-9, the inboard surface 824 of the leg faces the insertion axis 802 and extends from a leading end 836 to a trailing end 838 and the inboard surface 824 is spaced from the lower surface 816 a leading distance 840 near the leading end and a trailing distance 842 near the trailing end. In the example of FIGS. 45-50, the leading distance 840 is greater than the trailing distance 842 so that the lower face 816 and inboard surface 824 diverge in the leading direction defined by the leading end. When the implant 800 is inserted with the lower surface 816 adjacent a prepared tibial surface and the leg in a hole formed in the tibial bone, the implant will be secured against lifting off of the bone. Increasing insertion depth will result in increasing compression, as described relative to the example of FIGS. 1A-9, of the lower surface 816 against the prepared tibial surface due to the divergence of the lower surface and the leg.

Optionally, the leg may be removably attached to the spacer. The leg may be provided as a plurality of legs, the plurality of legs being interchangeable mountable relative to the spacer to provide a selectable size or shape of first leg. The leg may be engaged in sliding relationship to facilitate independent positioning of the articular component on the bone and adjusting of the compression created by the anchor component. For example, referring to FIGS. 47 and 48, the leg 822 may include a lengthwise slot 846 able to receive an enlarged edge 848 of the body. The leg 822 may slide lengthwise relative to the body but is prevented from moving distally away from the body 820 while the enlarged edge 848 is engaged with the slot 846. The enlarged edge may take any form known in the art for producing a mechanism that slides in one direction but is constrained in a transverse direction. Examples may include but are not limited to a dovetail, spline, key hole, key and keyway, or other form. The slot 846 may extend the full length of the leg 822 or only partway. The leg 822 may be trapped on the body 820 or it may be removable and replaceable in one or both of the leading direction or trailing direction. In the example of FIGS. 45-50, the leg 822 is slotted from the trailing end 838 partway toward the leading end 836. The leg 822 may be removed from the body by sliding it in the leading direction as seen in FIG. 48. The leading end of the slot 846 will abut the body 820 to prevent it from being removed in the trailing direction as seen in FIG. 49. The position of the leg 822 shown in FIG. 49 is the initial insertion position. FIG. 50 illustrates the leg having been driven forward to a subsequent position that will increase the compression of the lower surface 816 against the bone.

FIGS. 51 and 52 illustrate a hole forming guide 850 having a guide body 851. The guide is similar to that of FIGS. 10-14 including holes 852 having axes 854 for guiding a punch, drill or the like to form a bone hole for receiving the leg 822 and slots 856 for guiding a saw, chisel, or the like to form a bone slot for receiving the body 820. The guide 850 includes a probe 858 having a probe lower surface 860 engageable with the bone surface on which the tray lower surface 816 will rest to orient the holes 852 and slots 856 relative to the bone surface. In the example of FIGS. 51 and 52, the hole axes 854 diverge from the probe lower surface 860 at an angle equal to the divergence of the tray lower surface 816 and leg inboard surface 824. As described relative to the example of FIGS. 1A-9, the equal divergence of the hole and leg results in uniform compression over the length of the leg.

In use, the guide 850 is positioned with the probe lower surface 860 resting on the planar cut surface 870 of the tibia 872 and the guide body 851 abutting the anterior of the tibia as shown in FIG. 52. A drill 874, for example, is guided in the guide hole 852 to form a bone hole 876. A saw (not shown), for example, is guided in the slot 856 to form a bone slot 878 intersecting the bone hole 876 and the cut surface 870 of the tibia. The guide 850 is removed. Referring to FIG. 53, the implant 800, is pressed in the leading direction with the lower surface of the tray 816 in contact with the cut surface 870, the body 820 in the slot 878, and the leg 822 in the bone hole 876. As the implant is driven forward, the leg will engage the wall of the bone hole as described relative to the example of FIGS. 1A-9. As the implant tray 812 reaches its final position on the tibia it is compressed down against the tibial surface. Where an optional separate sliding leg 822 is provided, the tray 812 may be positioned at a desired location on the tibia and the leg 822 then driven to compress the tray 812 against the bone. This modular construction allows for independent positioning and compression. For example, where the lower bone engaging surface includes a fixation feature projecting from it, the lower bone engaging surface may first be engaged with the bone in a first direction transverse to the surface and then, without shifting the bone engaging surface across the bone, the leg may be advanced in a second direction transverse to the first direction to compress the bone engaging surface against the bone. A crossing screw may be placed through the optional aperture 880 if desired as described relative to the example of FIGS. 1A-9 such as by using the cross fixation guide 400 of FIG. 19. In another example, the optionally separate sliding leg may be positioned as shown in FIG. 49, with the leading end of the body 820 abutting the leading end 847 of the slot 846. As the implant is driven forward, e.g. by engaging a driver with a threaded hole 882 in the trailing end of the tray (FIG. 45), the abutting body 820 drives the leg 822 forward with it. Once the tray 812 is positioned as desired, a driver may be engaged with the trailing end of the leg 822 to drive the leg to compress the implant against the bone. To remove the implant 800, a removal tool, e.g. a slap hammer, may be engaged with the trailing end of the leg 822 and the leg withdrawn to reduce the compression and allow the implant to be removed. A driver or removal tool may engage the leg 822 via a threaded socket such as that shown in FIG. 9.

Figure 54:
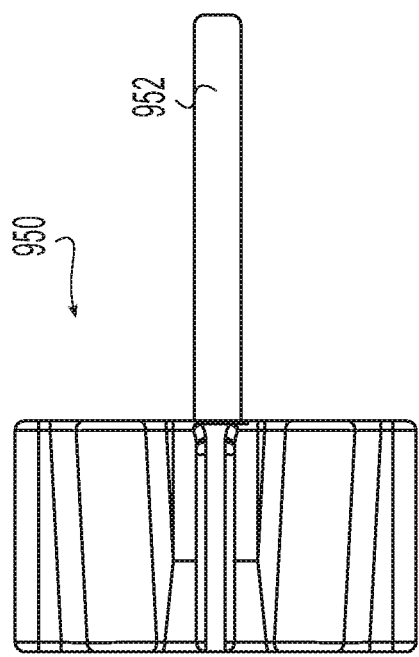
FIG. 54 is a side elevation view of an implant according to one example of the invention.

FIG. 54 illustrates another example of an implant 900 similar to that of FIGS. 1A-9. In the example of FIG. 54, the body 902 includes a spacer 904 that may be placed between bone portions to maintain them a desired distance apart and anchor portions, as described relative to the example of FIGS. 45-50, positioned on opposite sides of the spacer 904. The implant 900 of FIG. 54 is suitable, for example, for spacing and securing adjacent bone portions while they fuse together during healing. Examples of applications for such an implant include fusing adjacent vertebrae of the spine, joint fusions at other locations, osteotomy fusions, and the like where it is desired to fill a natural or surgically created gap between the bone portions. The spacer 904 may have planar, parallel opposing sides as shown or they may be shaped to fit the contours of the adjacent bone and/or to fill an angled gap. In the example of FIG. 54, the legs 906 include a through hole 908 that may receive a screw 910 axially. In the example of FIG. 54, only one screw is shown but one may be provided in both legs or not at all. The screw has a trailing head 912 and a leading thread 914. When the screw 910 is rotated, the threads engage the wall of the bone hole and the head abuts the trailing end of the leg to pull the leg 906 and thus the implant 900 forward into engagement with the bone. The screw 910 allows the implant 900 to be driven smoothly without impact forces. The screw also prevents the implant 900 from translating backward. The screw may be permanently trapped within the implant or it may be removably engaged. For example, the leg 906 may have a longitudinal slot through which the screw may be moved laterally to be engaged with or disengaged from the leg 906.

Figure 55:
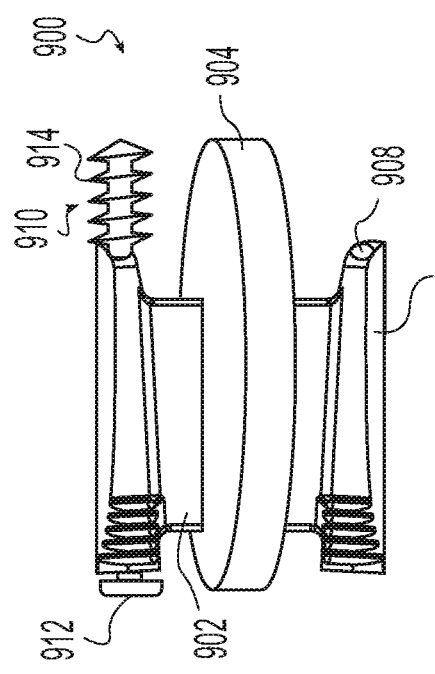
FIG. 55 is a side elevation view of an example of a hole forming guide for the implant of FIG. 54.

FIG. 55 illustrates a hole forming guide 950 similar to that of FIGS. 10-14 but having an additional probe 952 with a thickness equal to that of the spacer 904 and which is inserted between the bone portions to position them in the proper orientation relative to the guide 950.

Figure 57:
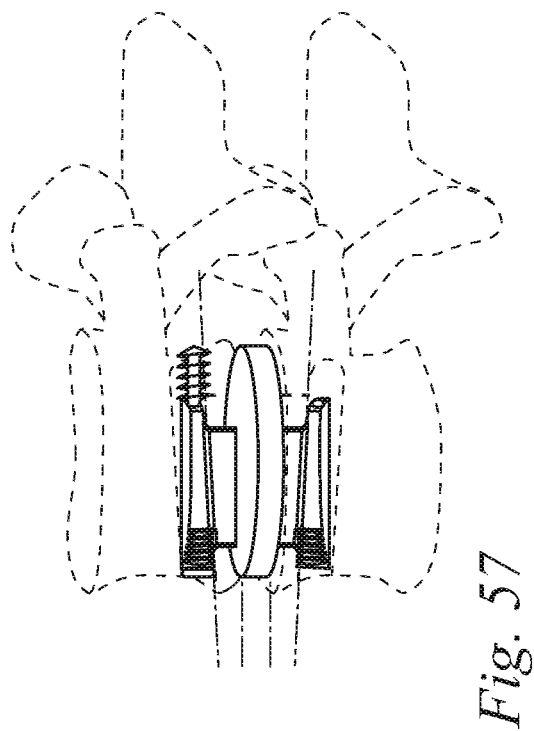
FIG. 57 is a side elevation view of the implant of FIG. 54 mounted to adjacent bones.
Figure 56:
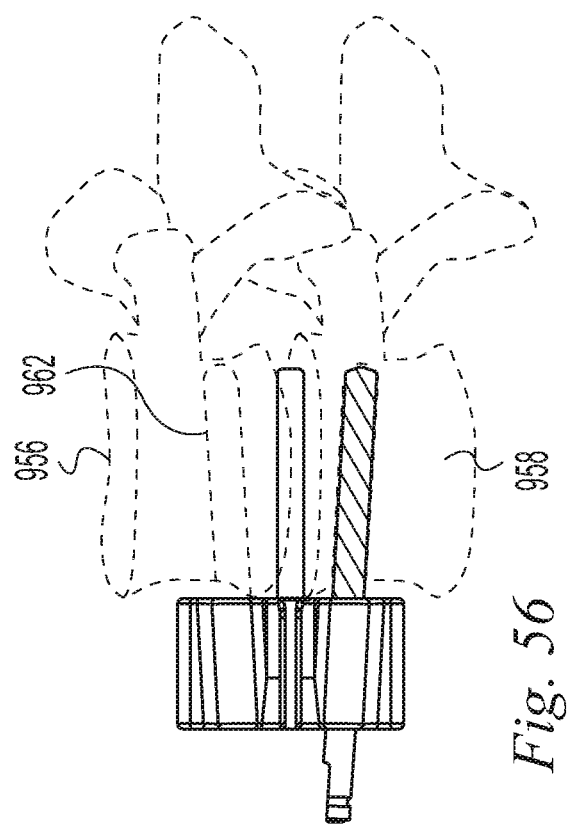
FIG. 56 is a side elevation view of the hole forming guide of FIG. 55.

FIGS. 56 and 57 illustrate an interbody fusion procedure using the guide 950 and implant 900. The guide is positioned with the probe 952 between the vertebrae 956, 958 and a hole 962 is formed in each bone portion. The guide 950 is removed and the implant 900 is inserted so that each bone portion is compressed against one of the opposing sides of the spacer 904.

Several illustrative examples have been shown. The various features of the different examples may be combined or substituted among the examples within the scope of the invention. For example, the independently sliding leg shown in the example of FIG. 45-50 may be used with the example of FIGS. 1A-9 or the example of FIG. 54. Likewise, the longitudinal screw of FIG. 54 may be used with the example of FIGS. 1A-9 or the example of FIGS. 45-50. Similarly, the threaded inserter 300 of FIGS. 15-18, the cross fixation guide 400 of FIG. 19, or the flexible member 502 of FIGS. 23-25 may be used with the example of FIGS. 45-50 or the example of FIG. 54.

Figure 58:
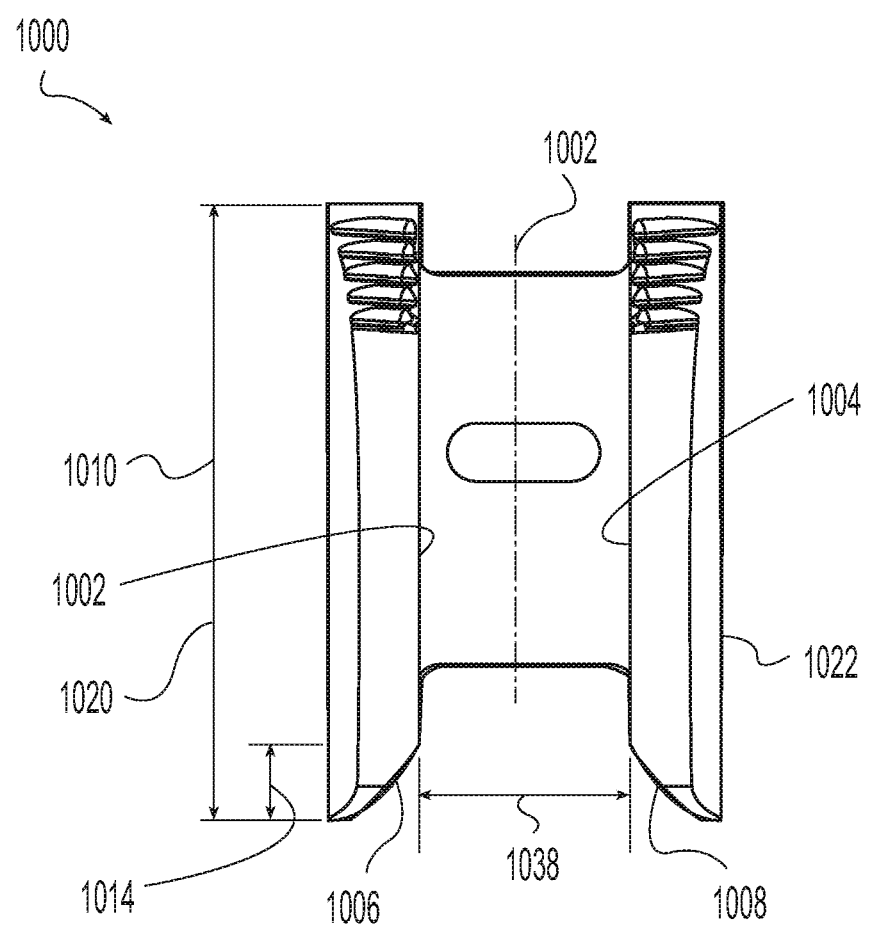
FIG. 58 is an elevation view of a bone implant according to one example of the invention.

Some of the preceding illustrative examples of the invention include fastener surfaces that diverge to cause compression upon engagement of the fastener with one or more bones. FIG. 58 depicts a fastener 1000 in the form of a staple similar to the fastener in the example of FIGS. 1A-9. However, in the example of FIG. 58, the inboard surfaces 1002 and 1004 of the legs are parallel. The leading end of each leg includes a relieved portion 1006, 1008 on the inboard side. The relieved portion may be in the form of a flat or radiused surface and serves to create compression as the fastener 1000 is inserted into holes formed in bone. The legs each have a length 1010 measured parallel to the insertion axis 1012. Likewise, the relieved portions each have a length 1014 measured parallel to the insertion axis 1012. The relieved portion length 1014 is preferably greater than 5% of the leg length 1010. More preferably the relieved portion length is in the range from 5% to 50% of the leg length. More preferably the relieved portion length is in the range from 10% to 30% of the leg length. More preferably the relieved portion length is in the range from 10% to 20% of the leg length. The relieved portions provide divergent ramps. Preferably the outer surfaces 1020, 1022 are parallel.

Figure 59:
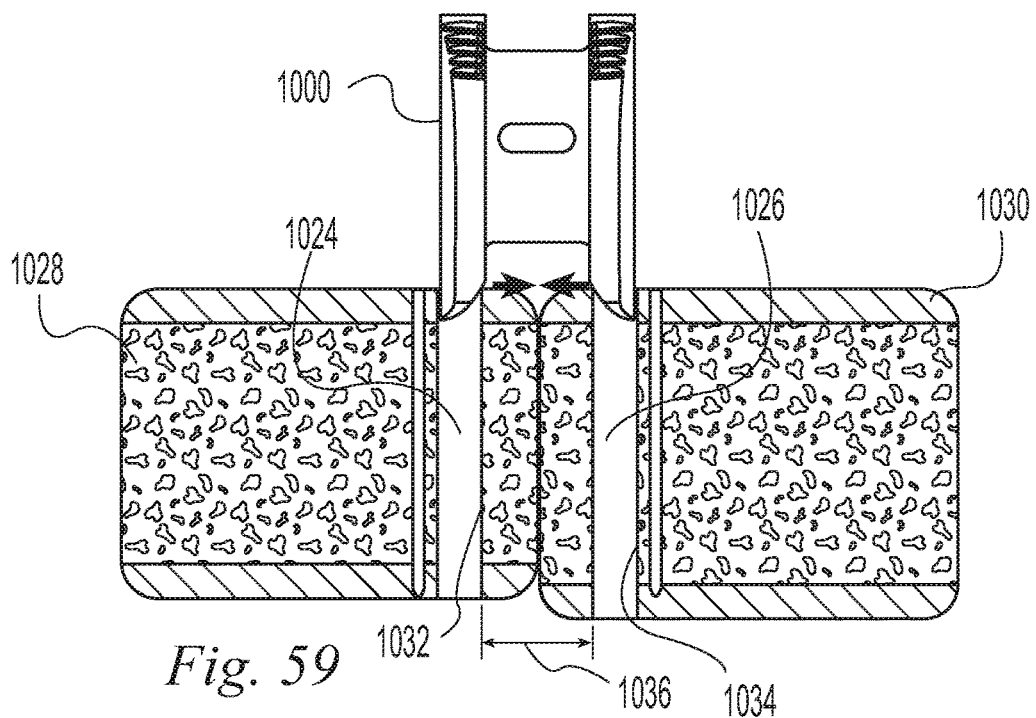
FIGS. 59-61 illustrate a surgical method according to one example of the invention utilizing the implant of FIG. 58.
Figure 60:
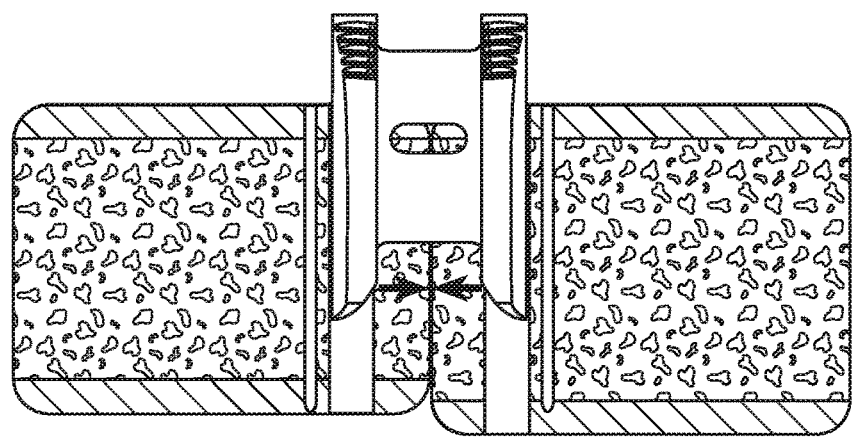
Figure 61:
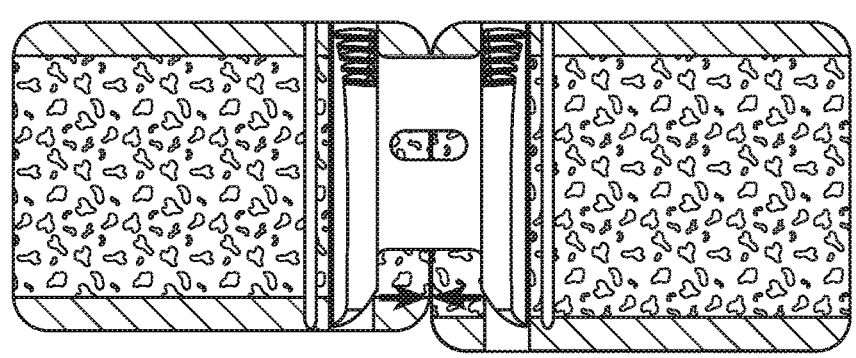

FIGS. 59-61 illustrate an example of a method of using the fastener 1000 of FIG. 58. In FIG. 59, bone holes 1024, 1026 have been formed at least partway through first and second bone portions 1028, 1030. The bone holes may be formed with a guide similar to the guide 200 of FIG. 26 but having parallel rather than divergent guide holes. The guide may also be used to guide the formation of a slot in the bone extending between the bone holes. The bone holes have inboard surfaces 1032, 1034. The bone hole inboard surfaces are spaced apart a distance X 1036. The inboard surfaces of the fastener legs are spaced apart a distance Y 1038. The bone holes 1024, 1026 are offset outwardly to create interference with the inboard surfaces of the legs, or in other words, X is greater than Y. Preferably the holes are sized so that the outer surfaces 1020, 1022 of the legs can slide freely within the holes. When the fastener legs are inserted into the bone holes, the relieved portions 1006, 1008 engage the inboard sides of the bone holes as shown in FIG. 59. With further insertion of the fastener legs, the bone portions are compressed between the fastener legs as shown in FIGS. 60 and 61. The parallel inboard surfaces 1002, 1004 of the legs trailing the relieved portions engage the compressed bone and maintain the compression.

Figure 62:
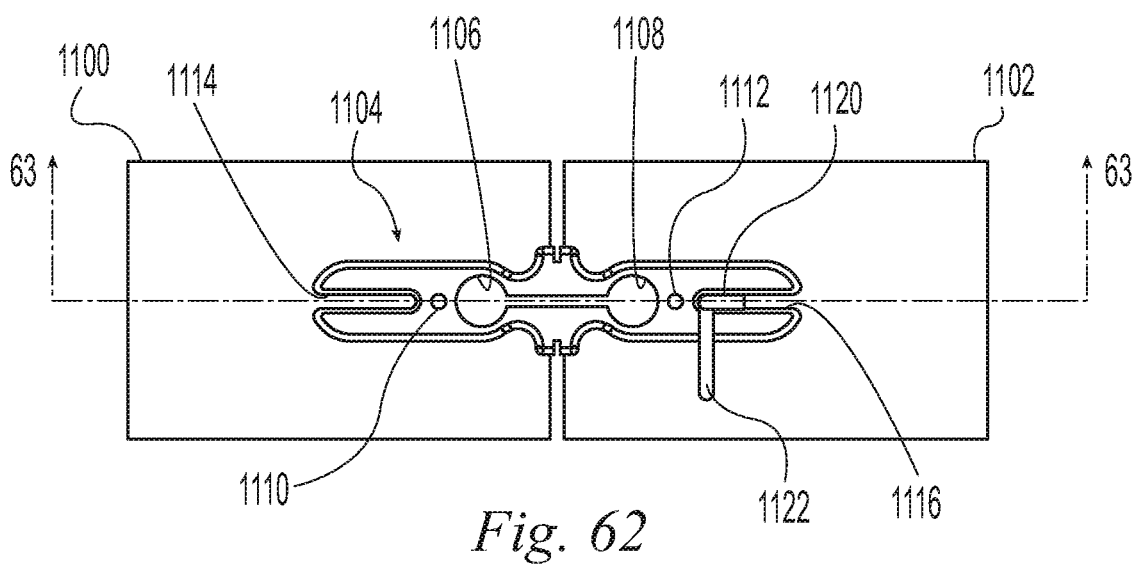
FIGS. 62-72 illustrate instruments and a surgical method according one example of the invention.
Figure 63:
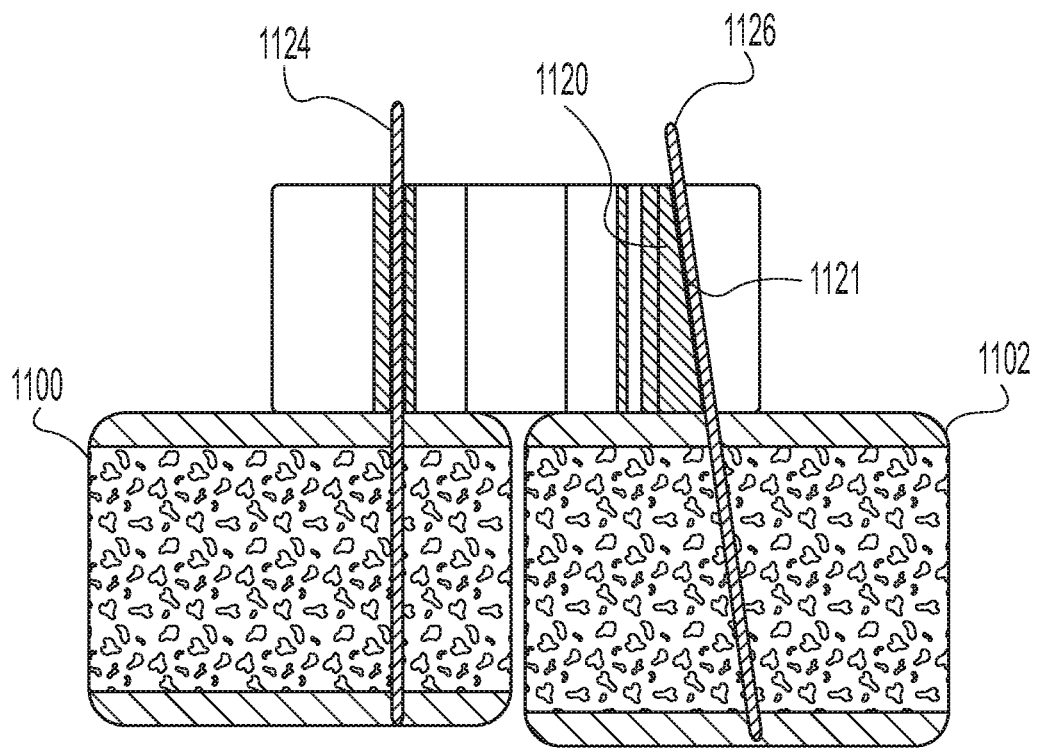

FIGS. 62-72 illustrate an example of a method in which instruments are used to compress first and second bone portions 1100, 1102 together prior to insertion of a staple with parallel legs. Referring to FIG. 62, a guide 1104 has been positioned on the first and second bone portions. The guide 1104 of FIG. 62 is similar to the guide 200 of FIG. 26. However, the guide 1104 of FIG. 62 has parallel guide holes 1106, 1108. Fixation holes 1110, 1112 formed through the guide are sized to receive fixation pins to secure the guide to bone. Slots 1114, 1116 formed collinear with the holes 1106, 1108, 1110, 1112 are also sized to receive fixation pins. A removable angle guide 1120 with a handle 1122 may be positioned within one of the slots 1114, 1116. The angle guide 1120 has a generally wedge-shaped body as shown in FIG. 63 providing a guide surface 1121 that diverges outwardly from the fixation holes 1110, 1112 in the direction toward the bone surface.

Referring to FIG. 63, the first and second bone portions have been aligned approximately in a desired orientation. A first fixation pin 1124 has been inserted into a fixation hole 1110 and into the first bone portion 1100. A second fixation pin 1126 has been inserted into a slot 1116 and into the second bone portion 1102 by guiding the second fixation pin 1126 along the angle guide 1120 to place the second fixation pin 1126 non-parallel to the first fixation pin 1124 with the pins diverging from one another in a direction into the bone.

Figure 64:
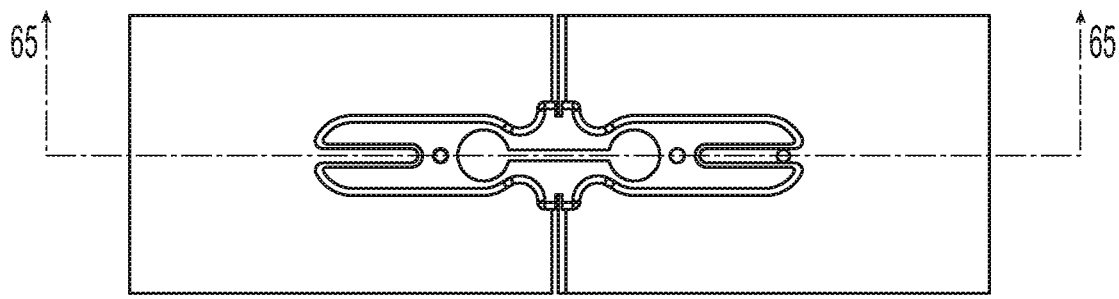
Figure 65:
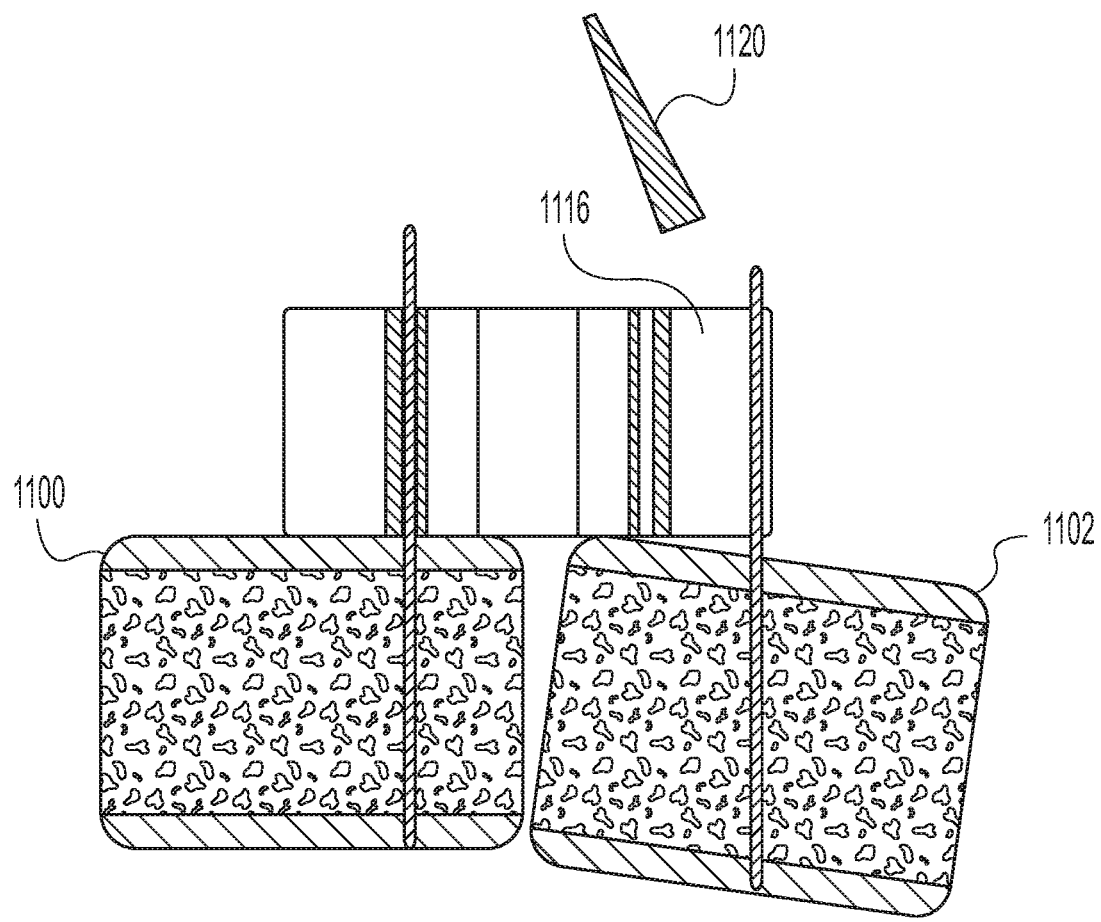

Referring to FIGS. 64 and 65, the bone portions 1102, 1104 have been rotated relative to one another to position the fixation pins parallel to one another. The angle guide 1120 has been removed from the slot 1116.

Figure 66:
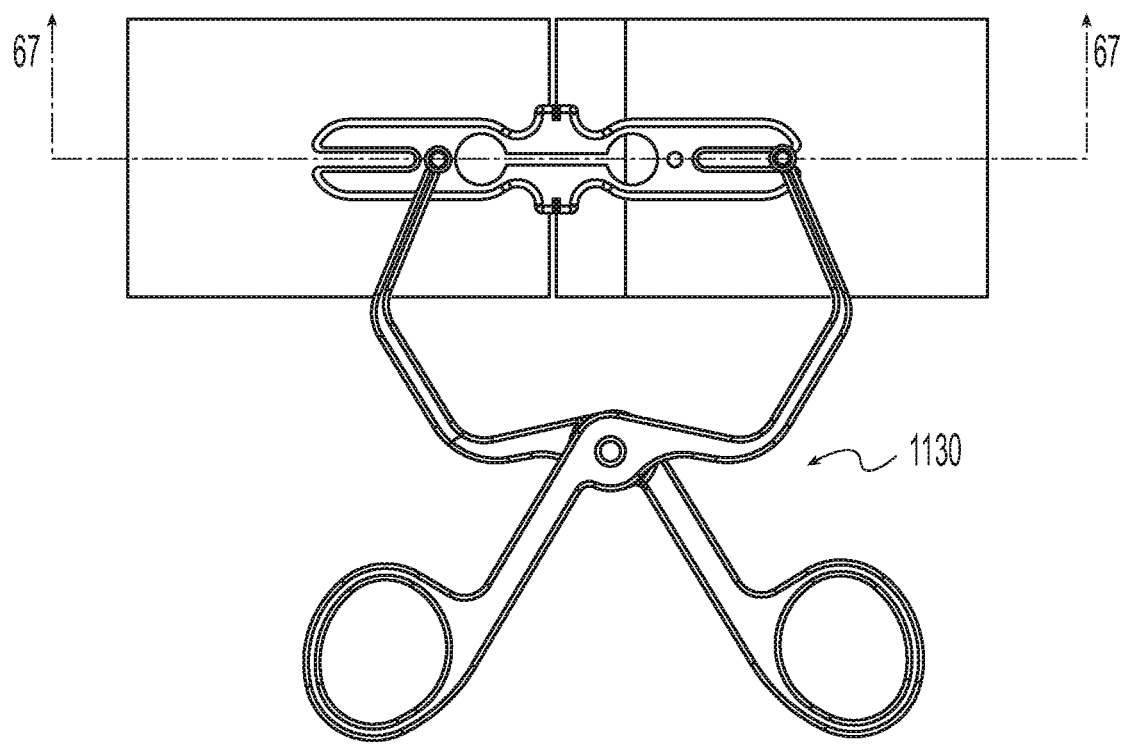
Figure 67:
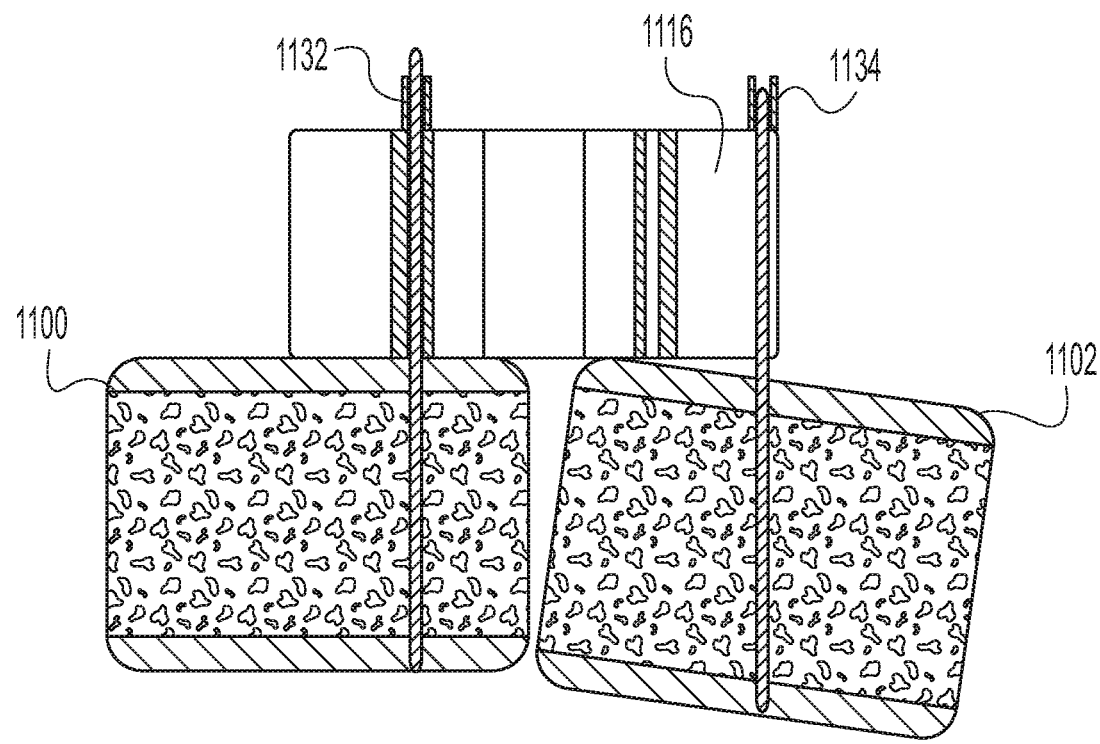

Referring to FIGS. 66 and 67, with the fixation pins parallel to one another, a compressor 1130 is engaged with the fixation pins. In the example of FIGS. 66 and 67, the compressor is engaged by sliding bushings 1132, 1134 on the end of compressor arms over the ends of the fixation pins. The compressor is then actuated to move the fixation pins, and consequently the first and second bone portions, toward one another. Referring to FIG. 67, when the compressor is actuated to move the bone portions together, one aspect of the bone portions will contact first due to the relative angle between the pins during insertion and the subsequent rotation of the bone portions to align the pins. In the example of FIGS. 62-72, the lower edges of the bone portions will contact first. With further compression, the bone portions will rotate into contact with one another at multiple points along the interface between the bone portions to a reduced position. The relative rotation between the bone portions causes one or both of the fixation pins to elastically deform in bending. With one of the pins in the slot 1116, the pin is allowed to translate within the slot as the pins move together.

Figure 68:
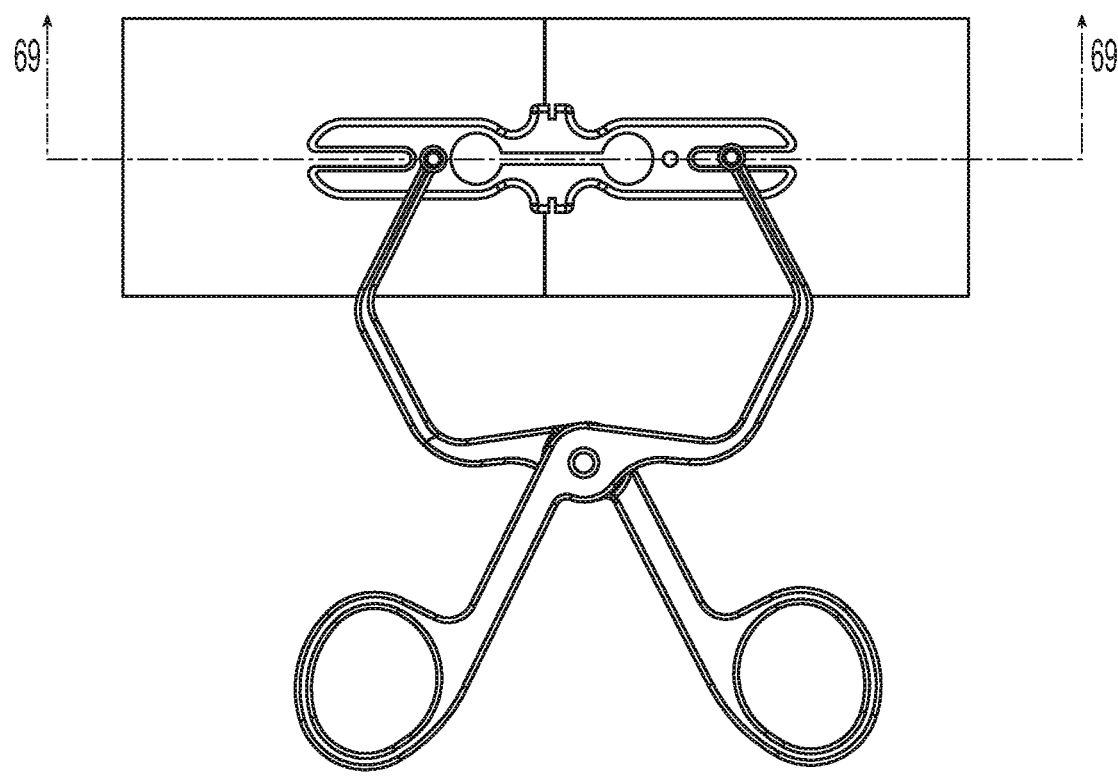
Figure 69:
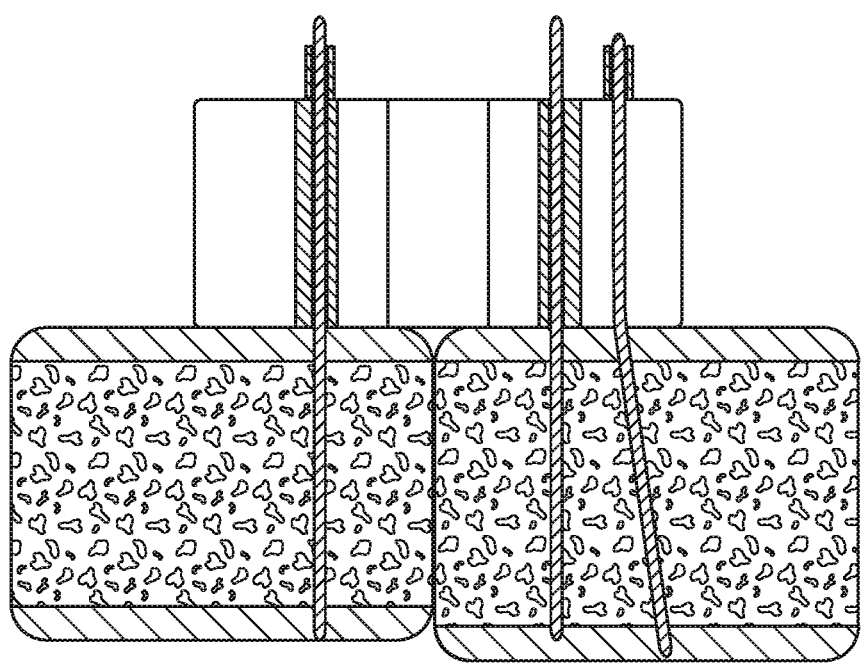

Referring to FIGS. 68 and 69, the bone portions have been moved together until they contact all along the bone interface. With the top edges of the bone portions in contact, the elasticity of the fixation pins imparts oppositely directed moments on the bone portions to ensure that the lower edges of the bone portions remain biased together.

Figure 70:
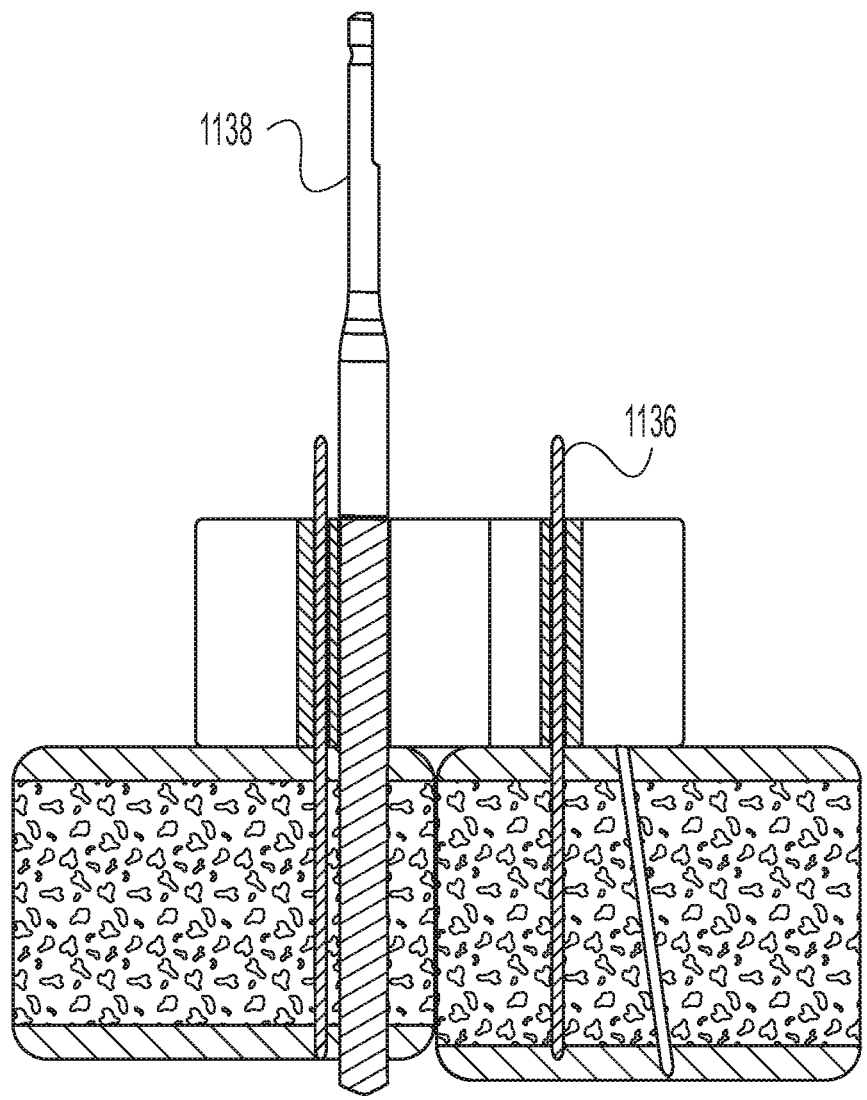

Referring to FIG. 70, a third fixation pin 1136 has been inserted into the second fixation hole 1112 in the guide to secure the bones in the reduced position and the second fixation pin 1126 has been removed. A drill 1138 is shown being guided by the guide holes 1106, 1108 to form bone holes.

Figure 71:
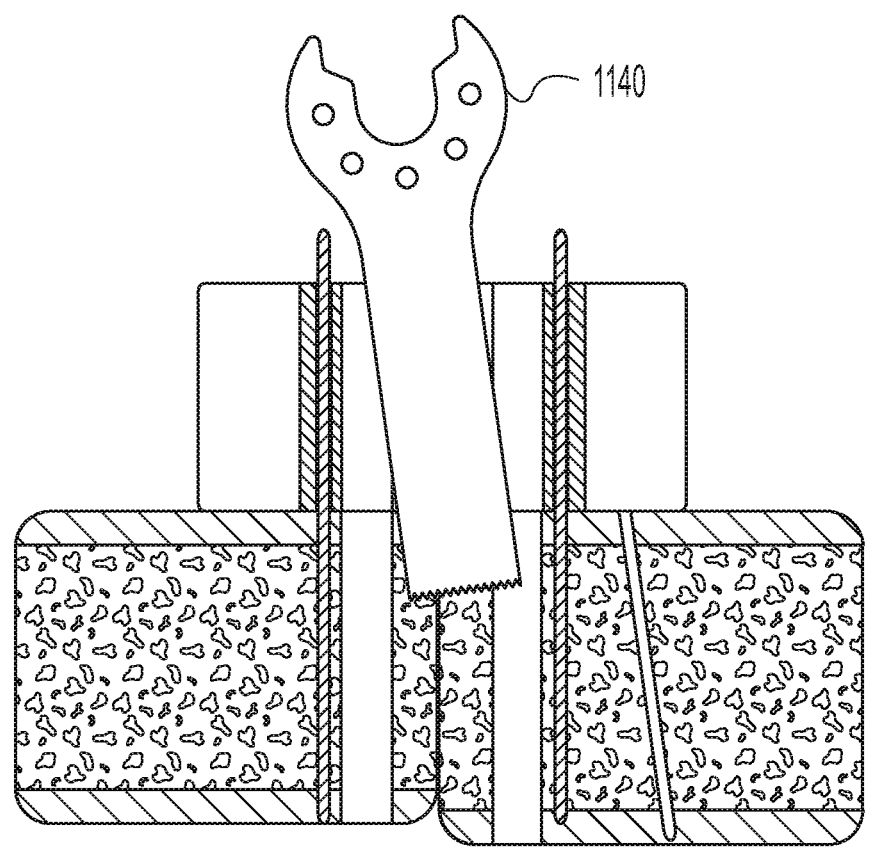

Referring to FIG. 71, a saw blade 1140 is guided by the guide to form a slot extending between the bone holes to receive the fastener body.

Figure 72:
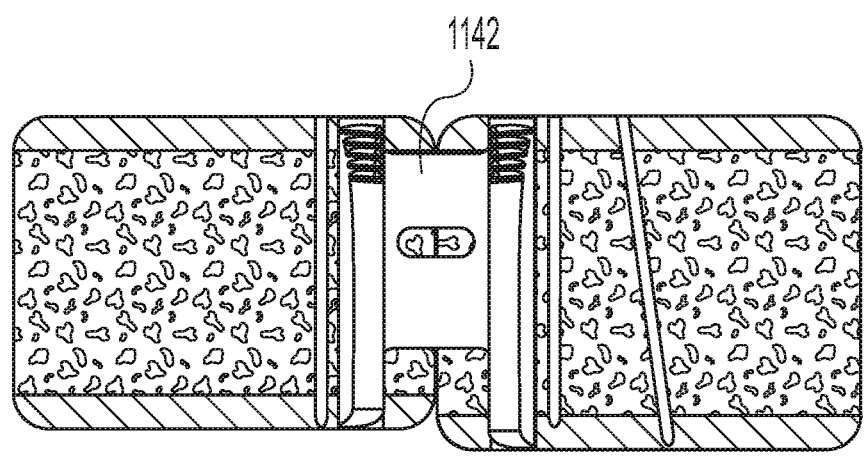

Referring to FIG. 72, a parallel legged fastener 1142, similar to that of FIG. 58 is inserted with a leg in each of the bone holes to secure the bones relative to one another. Because the legs are parallel, the fastener 1142 may be inserted through the guide. Alternatively, the guide may be removed before the staple is inserted. The guide may include removable inserts that may be inserted into the guide to provide guide surface for the drill and saw blade and then removed to provide clearance for inserting the staple through the guide.

Figure 73:
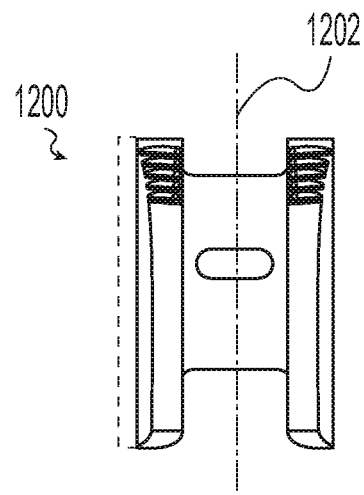
FIG. 73 illustrates an implant according to one example of the invention.

FIG. 73 illustrates an example of a fastener 1200 having parallel legs as in the example of FIG. 58. The fastener 1200 is formed of an elastic aterial so that it may be elastically deformed in a direction normal to the insertion axis 1202. The deformed configuration is shown in dashed lines and the relaxed state is shown in solid lines.

Figure 74:
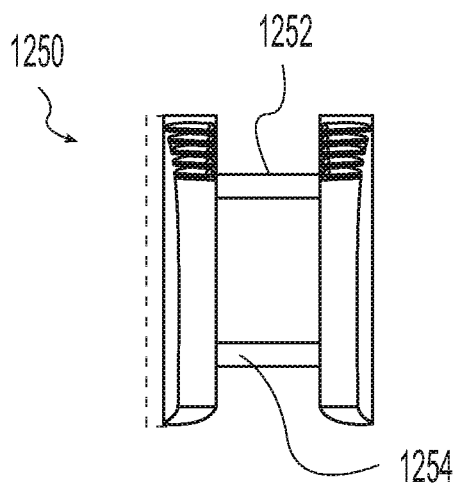
FIG. 74 illustrates an implant according to one example of the invention.

FIG. 74 illustrates another example of a fastener 1250 similar to the fastener 1200 of FIG. 73. Fastener 1250 of FIG. 74 differs from the fastener 1200 in that rather than having an implant body in the form of a web extending between the legs, the fastener 1250 has discrete bands 1252, 1254 of material extending between the legs. The fasteners 1200, 1250 may be made from any material having a suitable elastic deformation range. Preferably the fasteners 1200, 1250 are made from a superelastic material. An example of a suitable superelastic metallic material is superelastic nitinol. In use, the fasteners are elastically deformed by displacing the legs outwardly normal to their insertion axes and held in the deformed state while they are inserted. After insertion, into the bone portions, the legs are released and the legs move back toward their relaxed state compressing the bone portions between them.

Figure 75:
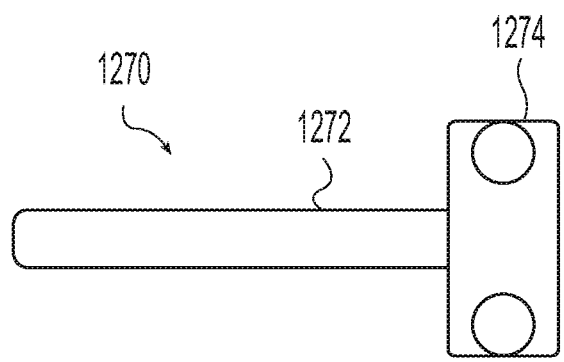
FIGS. 75-77 illustrate an instrument according to one example of the invention for use with the implants of FIGS. 73 and 74.
Figure 76:
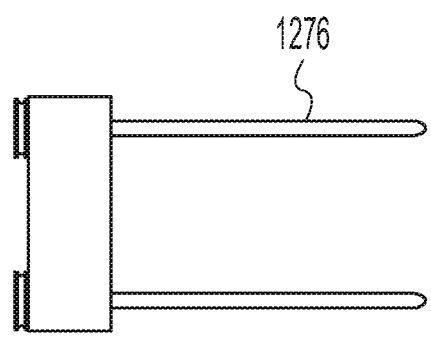
Figure 77:
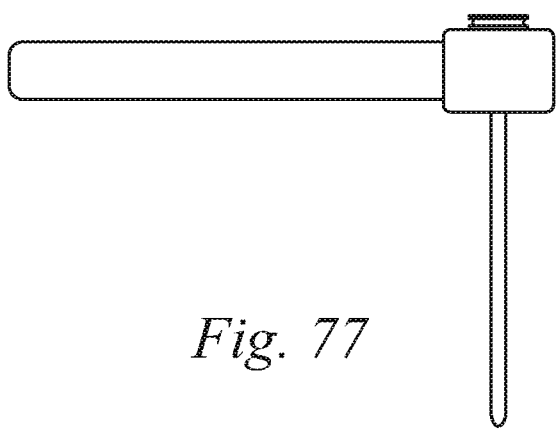

FIGS. 75-77 illustrate an example of an inserter 1270 for use with the fasteners of FIGS. 73 and 74. The inserter 1270 includes a handle 1272 and a head 1274. The head includes spaced apart holes that receive rigid pins 1276 extending from the head. In use, a fastener is deformed by pulling the legs away from one another and sliding the rigid pins into the legs to keep them separated. Preferably a fastener is provided pre-mounted on the inserter 1270.

Figure 78:
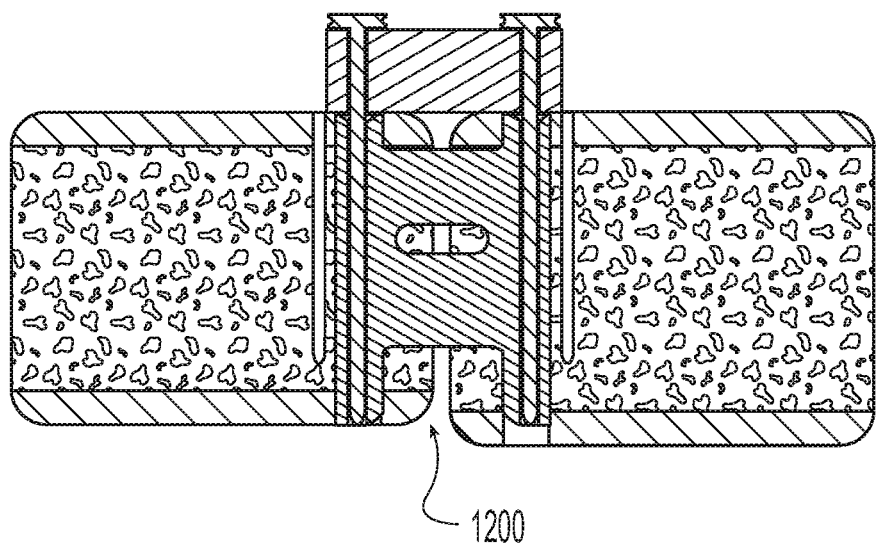
FIGS. 78 and 79 illustrate a surgical method according to one example of the invention utilizing the implants and instruments of FIGS. 73-77.

Referring to FIG. 78, a fastener and inserter assembly has been installed into predrilled holes in the bone portions.

Figure 79:
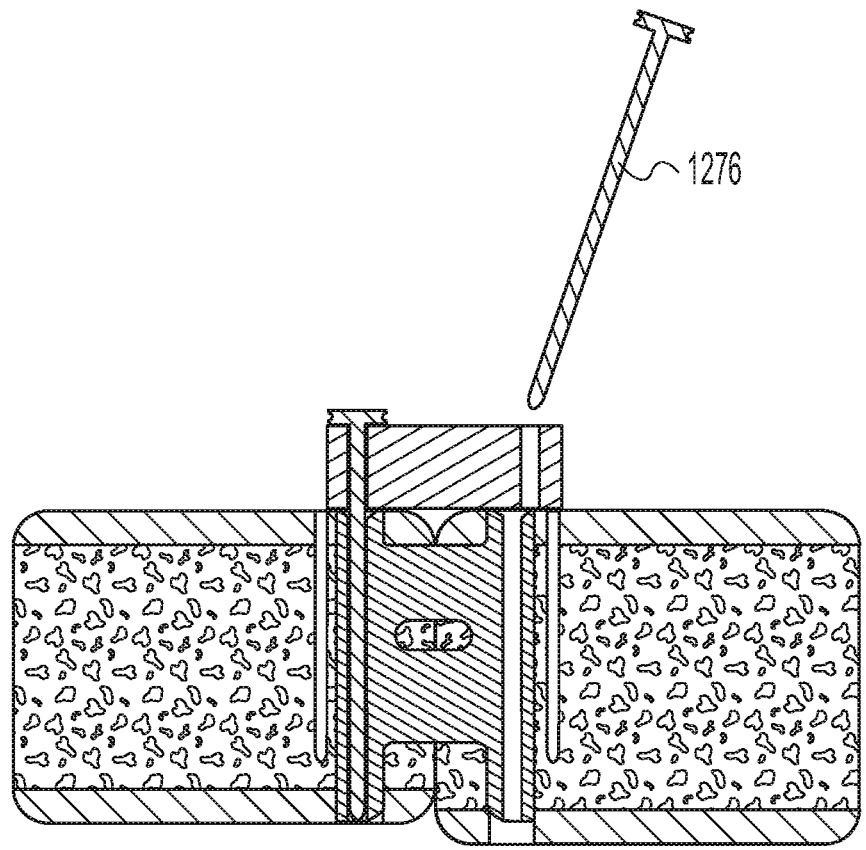

Referring to FIG. 79, one of the pins has been withdrawn from the inserter to allow the fastener to return toward its relaxed state and compress the bone portions together.

Features of the illustrative examples of FIGS. 58-79 may be substituted or combined with features of the examples of FIGS. 1-57 to form additional examples within the scope of the invention. For example, the examples of FIGS. 58-79 may be used to treat various conditions of the feet, hands, knees, spine and other locations as shown and described relative to the examples of FIGS. 1-57. The examples of FIGS. 58-79 may be combined with the examples of FIGS. 1-57 to provide a parallel leg fasteners with supplemental screw fixation passing through the body of the fastener and/or with joining elements connecting them and/or in the form of articular implants and/or in the form of joint fusion implants that achieve compression by way of relieved leading tips, instrumented compression, and/or elastic implant elements.

What is claimed is:

1. A method of stabilizing a first bone portion relative to a second abutting bone portion, the method comprising:
    providing a bone fastener having an insertion axis; a body; a first leg connected to the body; and a second leg connected to the body;
    inserting a first pin, having a first pin longitudinal axis, into the first bone portion;
    inserting a second pin, having a second pin longitudinal axis, into the second bone portion;
    engaging a compressor with the first and second pins;
    moving the first and second pins toward one another with the compressor to move the first and second bone portions toward one another;
    after moving the first and second bone portions toward one another, using a guide to guide the formation of a first hole from a surface of the first bone portion distally into the first bone portion, the first hole defining a first hole axis;
    using the guide to guide the formation of a second hole from a surface of the second bone portion distally into the second bone portion, the second hole defining a second hole axis, the first and second hole axes being positioned relative to one another in a predetermined relationship determined by the guide; and
    inserting the bone fastener with the first leg in the first hole and the second leg in the second hole.

2. The method of claim 1 further comprising using the guide to guide a cutter to form a slot extending from a portion of the first hole to a portion of the second hole to receive the body.

3. The method of claim 1 further wherein the first and second pins are inserted so that their axes are not parallel and are in a first relative angular orientation.

4. The method of claim 3 further comprising guiding the insertion of the first and second pins with the guide.

5. The method of claim 4 further comprising engaging a removable angle guide with a slot in the guide; guiding at least one of the first and second pins with the angle guide to orient the pin axes so that they are not parallel.

6. The method of claim 5 further comprising removing the angle guide from the guide after it is used to guide a pin and before moving the first and second pins toward one another with the compressor.

7. The method of claim 3 wherein moving the first and second pins toward one another with the compressor comprises elastically deforming at least one of the first and second pins.

8. The method of claim 7 further comprising translating at least one of the first and second pins within a slot in the guide when the first and second pins are moved toward one another.

9. The method of claim 7 wherein at least one of the first and second pins begins to deform after the first and second bone portions are in contact at a first contact point and continues to deform until the first and second bone portions are in contact at a second contact point.

10. The method of claim 3 further comprising before engaging the compressor with the first and second pins, repositioning the bones to change the relative angle between the pin axes.

11. The method of claim 10 further comprising before engaging the compressor with the first and second pins, repositioning the bones so that the pin axes are parallel.

12. The method of claim 1 wherein moving the first and second pins toward one another with the compressor to move the first and second bone portions toward one another comprises positioning the first and second bone portions so that they contact at a first contact point in a first state, moving the first and second bone portions toward one another until they contact at a second contact point in a second state, wherein the angular position between the first and second bone portions in the first state is different than the angular position between the first and second bone portions in the second state, wherein moving the first and second bone pins toward one another with the compressor further comprises elastically deforming at least one of the first and second pins while moving the first and second portions between the first and second states, the at least one elastically deformed pin exerting an elastic compressive force on the first and second bone portions.

13. The method of claim 12 wherein the at least one elastically deformed pin induces oppositely directed relative rotational moments on the first and second bone portions.

14. The method of claim 12 wherein in the first state, the first and second bone portions are in contact at the first contact point and have a gap between them opposite the first contact point and wherein in the first state the gap is reduced.

15. The method of claim 14 wherein the gap is reduced due to rotation of one bone portion relative to the other bone portion.

16. The method of claim 1 further comprising viewing a radiographic image of the first and second pins within the first and second bone portions as an approximation of the position the bone fastener will assume in the first and second bone portions.

17. The method of claim 16 further comprising after viewing a radiographic image of the first and second pins within the first and second bone portions as an approximation of the position the bone fastener will assume in the first and second bone portions, repositioning at least one of the pins to a more desirable position.

18. A method of stabilizing a first bone portion relative to a second abutting bone portion, the method comprising:
    providing a bone fastener having an insertion axis; a body; a first leg connected to the body; and a second leg connected to the body;
    positioning the first and second bone portions in an approximate final reduced position;
    positioning a guide on the approximately reduced first and second bone portions;

guiding a first pin into the first bone portion with the guide, guiding a second pin into the second bone portion with the guide, engaging a compressor with the first and second pins;

moving the first and second pins toward one another with the compressor to move the first and second bone portions toward one another, by elastically deforming at least one of the first and second pins while moving the first and second bone portions, the at least one elastically deformed pin exerting an elastic compressive force on the first and second bone portions;

after moving the first and second bone portions toward one another, using the guide to guide the formation of a first hole from a surface of the first bone portion distally into the first bone portion, the first hole defining a first hole axis;

using the guide to guide the formation of a second hole from a surface of the second bone portion distally into the second bone portion, the second hole defining a second hole axis, the first and second hole axes being positioned relative to one another in a predetermined relationship determined by the guide; and inserting the bone fastener with the first leg in the first hole and the second leg in the second hole.

19. The method of claim 18 further comprising translating at least one of the first and second pins within a slot in the guide when the first and second pins are moved toward one another.

20. The method of claim 18 further comprising using the guide to guide a cutter to form a slot extending from a portion of the first hole to a portion of the second hole, wherein inserting the bone fastener comprises inserting the body into the slot extending from the portion of the first hole to the portion of the second hole.

* * * * *